(12) United States Patent
Ulrich et al.

(10) Patent No.: US 8,476,461 B2
(45) Date of Patent: Jul. 2, 2013

(54) DIPYRROMETHENE-BORON HYDROPHILIC FLUORESCENT COMPOUNDS

(75) Inventors: Gilles Ulrich, Strasbourg (FR);
Raymond Ziessel, Souffelweyersheim (FR); Song-Lin Niu, Illkirch (FR);
Alexandre Haefele, Ostwald (FR);
Thomas Bura, Teting sur Nied (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 13/142,845

(22) PCT Filed: Dec. 18, 2009

(86) PCT No.: PCT/FR2009/052606
§ 371 (c)(1),
(2), (4) Date: Sep. 26, 2011

(87) PCT Pub. No.: WO2010/076516
PCT Pub. Date: Jul. 8, 2010

(65) Prior Publication Data
US 2012/0009615 A1    Jan. 12, 2012

(30) Foreign Application Priority Data
Dec. 29, 2008  (FR) ...................... 08 59098

(51) Int. Cl.
*C07D 209/56* (2006.01)
*C07F 5/02* (2006.01)
*G01N 21/76* (2006.01)

(52) U.S. Cl.
USPC ............. 548/405; 435/29; 436/501; 436/172; 250/459.1

(58) Field of Classification Search
USPC ... 435/29; 548/405; 436/501, 172; 250/459.1
See application file for complete search history.

(56) References Cited

U.S. PATENT DOCUMENTS
7,897,786 B2 *   3/2011  Ulrich et al. .................. 548/405

FOREIGN PATENT DOCUMENTS
WO    WO 2006/087459 A2    8/2006

* cited by examiner

*Primary Examiner* — Kahsay T Habte
(74) *Attorney, Agent, or Firm* — Knobbe Martens Olson & Bear, LLP

(57) ABSTRACT

Dipyrromethene-boron hydrophilic fluorescent compounds
The invention concerns fluorescent and hydrophilic compounds meeting following formula (I):

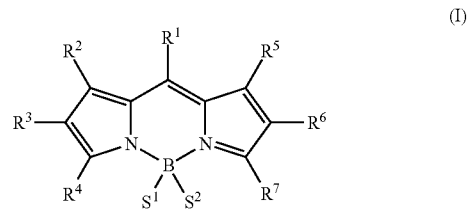

wherein:
$S^1$ is a group of formula —C≡C-L'-A where L' is a linkage group and A is a polar functional group;
$S^2$ is a —C≡C-L'-A group the same or different from $S^1$; —F; —H; or a hydrocarbon chain optionally interrupted by one or more oxygen atoms,
and use thereof, in particular in aqueous or hydrophilic media.

16 Claims, No Drawings

DIPYRROMETHENE-BORON HYDROPHILIC FLUORESCENT COMPOUNDS

The present invention concerns novel hydrophilic fluorescent compounds, used in particular as fluorescent markers in aqueous or hydrophilic media, which prove to be particularly adapted for use in biological media or for grafting on hydrophilic substrates (metallic oxides, organic polymers for example).

Fluorescent compounds are known in particular from international application WO2006/087459, which concerns unsaturated dipyrromethene-boron borocarbons having a large Stokes shift, which are useful as fluorescent markers, in particular for analysis by fluorescence or electroluminescence.

There is a need for fluorescent compounds of this type which further have a hydrophilic nature and are able to be used as markers in an aqueous medium for example. It would effectively be interest to be able to conduct fluorescence analysis methods in an aqueous medium, in particular for the study of biological processes, for fluoroimmmunological assay, fluorescence microscopy, flow cytometry, DNA sequencing and the marking of biological material. Yet, it is found that numerous fluorescent compounds which are useful as markers prove to be unusable in an aqueous medium. This is particularly the case with the compounds disclosed by WO2006/087459.

In addition, the modification of an insoluble fluorescent compound by a group capable of increasing the hydrophilic nature thereof does not systematically lead to obtaining a compound that can be used in practical terms in an aqueous or hydrophilic medium. On the contrary, experience has shown that the presence of a polar group on the dipyrromethene ring of the unsaturated dipyrromethene-boron borocarbons in WO2006/087459 does not systematically impart a water-soluble nature or even hydrophilic nature to the compound. In practice, it is observed that said compounds grafted by some polar groups on the dipyrromethene ring in fact aggregate in aqueous or hydrophilic media, which is probably accounted for by hydrophobic interactions between the dipyrromethenes or by specific interactions of hydrogen bonding type. This aggregating or intermolecular interaction leads extinguishing of luminescence.

It is one objective of the present invention to provide compounds which are useful as fluorescent markers and which can be used in hydrophilic media, and preferably in aqueous media without leading to the aforementioned phenomenon of aggregation.

For this purpose, the invention provides hydrophilic fluorescent compounds meeting following formula (I):

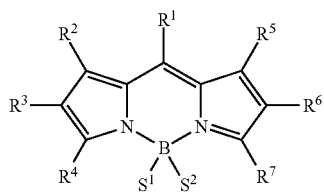

(I)

wherein:
S$^1$ is a group of formula —C≡C-L'-A, in which:
L' is a linkage group which is
a single bond (in which case S$^1$ is a group of formula —C≡C-A); or
a divalent hydrocarbon group chosen from the group consisting of straight or branched alkylenes, optionally comprising one or more oxygen, nitrogen or sulphur atoms in their chain (such as polyethylene glycol, polyethoxy or polypropoxy groups for example); straight or branched alkenylenes; straight or branched alkynylenes, and arylenes; or a divalent hydrocarbon chain formed by a chain of at least two divalent hydrocarbon groups of the aforementioned type;
A is a polar functional group chosen from among the sulphonate, sulphate, phosphate, ammonium, carboxylate, hydroxyl, phosphonate, alkylammonium sulphate and polyoxyethylene groups;
S$^2$ is:
a —C≡C-L'-A group the same or different from S$^1$, where L' and A have the aforementioned meanings;
—F;
—H; or
a hydrocarbon chain, straight or branched, saturated or unsaturated, optionally interrupted by one or more atoms of oxygen, nitrogen or sulphur, optionally cyclized in full or in part, optionally aromatic and optionally functionalized, and
each of the groups R$^1$, R$^2$, R$^3$, R$^4$, R$^5$, R$^6$ or R$^7$ each independently designates an —H group or a straight or branched, saturated or unsaturated hydrocarbon chain, optionally interrupted by one or more oxygen atoms, optionally cyclized in whole or in part, optionally aromatic and optionally functionalized,
on the understanding that all or part of the groups R$^1$, R$^2$, R$^3$, R$^4$, R$^5$, R$^6$ and R$^7$, may be linked together to form a bridged form (i.e. at least two of the groups R$^1$, R$^2$, R$^3$, R$^4$, R$^5$, R$^6$ et R$^7$ may together form a ring with the carbons with which they are linked).

The compounds meeting formula (I) above are hydrophilic, namely they are capable of creating bonds with the molecules of water, in particular hydrogen and/or ionic bonds, or strong polarity. For some of the compounds of the invention, the hydrophilic nature is sufficient to ensure water-solubility. In particular, numerous compounds according to the invention have a water solubility of a least 0.1 mg/L, and some have a water solubility equal to or more than 1 mg/L, even more than 5 mg/L, for example equal to or more than 10 mg/L.

With the present invention, the inventors have now evidenced that a compound meeting the above-mentioned formula (I), in which at least one of the groups present on the boron comprises a polar group, is hydrophilic and does not lead to phenomena of aggregation when placed in a hydrophilic or aqueous medium, which allows use therefore in particular as fluorescent marker in a hydrophilic or aqueous medium. This result is unexpected in the light of the results observed with the unsaturated dipyrromethene-boron borocarbons in WO2006/087459 comprising a polar group on the dipyrromethene ring, cited above in the present description, for which no such effect is observed. The observed effect appears, at least in part, to be explained by the fact that the substitution at the boron by one or more hydrophilic groups prevents the formation of aggregates, the molecule becoming more hindered and hence less likely to aggregate.

In addition, the hydrophilic function(s) added at the boron centre of the compounds according to the invention impart chemical stability to the compounds that is greater than that of similar difluorinated compounds (S$^1$=S$^2$=F). This stability allows the use of the compounds according to the invention for marking molecules which may undergo subsequent chemical synthesis steps (peptide synthesis, oligonucleotide synthesizer for example), but also allows the incorporation of the compounds of the invention in optoelectronic devices (OLEDs—organic light-emitting diodes) and photovoltaic cells.

In general, the variations of groups $R^1$, $R^2$, $R^3$, $R^4$, $R^6$ and $R^7$ allow modulation of the emission wavelength of the compounds.

Different aspects and preferred embodiments of the invention will now be described in more detail.

By "hydrocarbon chain" in the meaning of the present description is meant a chain comprising one or more carbon atoms and one or more hydrogen atoms, this chain being functionalized or non-functionalized. The hydrocarbon chains present in the compound of formula (I) according to the invention preferably comprise 1 to 8 carbon atoms, preferably less than 6 carbon atoms. In the present description when reference is made to a "functionalized chain," it is meant that the chain comprises at least one functional group.

By "alkylene" is meant herein a divalent saturated hydrocarbon radical, with straight or branched chain, preferably comprising 2 to 10 carbon atoms, for example 3 to 6 carbon atoms. For example, mention may be made of the following straight or branched radicals: methylene, ethylene, propylene, butylene, pentylene, hexylene, octylene, nonylene, decylene, dodecylene, hexadecylene and octadecylene. In the meaning of the present description, the term "alkylene" also encompasses the groups of the type mentioned above further including oxygen atoms. Polyethylene glycol and polypropylene glycol are the preferred straight alkylenes comprising several oxygen atoms.

By "alkenylene" is meant a divalent hydrocarbon radical comprising at least one ethylene unsaturation (typically one or more >C=C< bonds, which may or may not be adjacent), preferably comprising 2 to 8 carbon atoms, for example 3 to 6 carbon atoms. As examples of alkenylene radicals, particular mention may be made of allylene or vinylene radicals.

By "alkynylene" is meant a divalent hydrocarbon radical comprising at least one acetylene unsaturation (typically one or more —C≡C— bonds).

By "arylene" is meant an aromatic divalent hydrocarbon radical, with one or more rings fused or non-fused, particularly having 4 to 16 carbon atoms, preferably 4 to 10 carbon atoms, and possibly containing nitrogen, sulphur or oxygen atoms in their ring (heterocycles). The aryl groups are optionally substituted by one or more alkyl or alcoxy groups, in particular by methyl or methoxy. Amongst the aryl radicals, particular mention may be made of phenyl, naphtyl, pyrenyl, perylenyl, anthracenyl, thienyl, pyrolyl, pyridinyl or furanyl radicals.

According to one particular embodiment, the $R^3$ and $R^4$ groups together form a divalent group and/or the two groups $R^6$ and $R^7$ together form a divalent group. In this case, said divalent groups are preferably such that with the carbon atoms with which they are attached they form a structure chosen from the group consisting of one cycle or two condensed rings, each ring having 5 or 6 atoms and comprising carbon atoms and optionally heteroatoms (preferably 1 to 3 when applicable) chosen from among N, O and S.

According to one embodiment of interest, each of the groups $R^1$, $R^2$, $R^3$, $R^4$, $R^5$, $R^6$ et $R^7$ each independently designates a group chosen from among the groups of formula —H; -L—H, -G or -L-G, in which:

G is a functional group, preferably chosen from among the amine, amide, carboxylic acid, ester, sulphonate, sulphate, phosphate, ammonium, hydroxyl, phosphonate and polyoxyethylene groups, L is a linkage group consisting of one or more segments chosen from among a single bond; straight or branched alkylenes optionally comprising one or more oxygen atoms in their chain; straight or branched alkenylenes; alkynylenes, and arylenes; the L group possibly carrying at least one functional group in addition to the G group; this functional group possibly being the same or different from the G group. More generally, when L carries several functional groups, these groups may each be the same or different and are preferably chosen from among the amine, amide, carboxylic acid, ester, sulphonate, sulphate, phosphate, ammonium, hydroxyl, phosphonate and polyoxyethylene groups.

When several groups $R^1$, $R^2$, $R^3$, $R^4$, $R^5$, $R^6$ and $R^7$ meet the definition -G or -L-G, the G groups may be the same or different.

Preferably, the functional group A present on the —C≡C-L'-A group as $S^1$ group in the formula (I) compounds is chosen from among the polyoxyethylene, phosphate, sulphate and alkylammonium sulphate groups, which imparts a particularly pronounced hydrophilic, even water-soluble nature to compound (I). When the compound (I) carries a $S^2$ group meeting the formula —C≡C-L'-A, it is preferable for the functional A group to be chosen from among the aforementioned polar groups, which further tends to strengthen the hydrophilic nature obtained.

According to one advantageous embodiment, in the formula (1) compounds the $S^1$ and $S^2$ groups are both groups which meet the above-mentioned formula —C≡C-L'-A (in which L' and A have the aforementioned meanings). In this embodiment, compound (I) comprises two groups on the boron which each comprise a polar A group. Therefore, the compounds according to this embodiment in general have an enhanced hydrophilic nature.

Preferably, in the compounds of the invention, the $S^1$ and $S^2$ groups are the same.

According to one particular embodiment, in the formula (1) compounds of the invention, the $S^1$ group (and optionally the $S^2$ group) comprises a polyoxyethylene group. According to this embodiment, advantageously the $S^1$ group, as -L-A group, comprises a group of formula —(—O—$CH_2$—$CH_2$)$_n$—O—S', and the hydrophilic and fluorescent compound of the invention then meets the following formula (II):

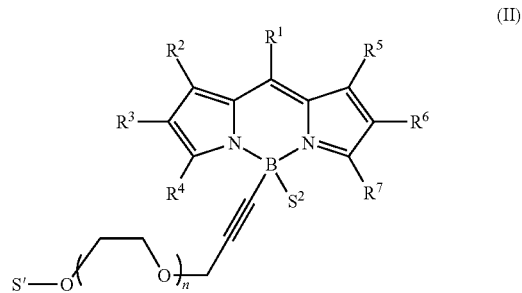

(II)

wherein:
$R^1$, $R^2$, $R^3$, $R^4$, $R^5$, $R^6$, $R^7$ and $S^2$ are such as defined above,
n is 1, 2, 3 or 4,
S' is —H, -Me —$(CH_2)_{n'}$—$SO_3^-(X^{m+})_{1/m}$ ot —$(CH_2)_{n'}$—$PO_3^{2-}(X^{m+})_{2/m}$ in which:
$X^{m+}$ is a cation (mono- or polyatomic) of valence m (this valence M typically being 1, 2, 3 or 4),
n' is an integer of 1, 2, 3 or 4.

The cations $X^{m+}$ of formula (II) are preferably cations of alkaline metal, alkaline-earth metal or quaternary ammonium cations.

More generally, when mention is made of cations associated with the compounds of the invention in the present description, these cations X are preferably alkaline metal, alkaline-earth metal or quaternary ammonium cations, typically cations chosen from among $Li^+$, $Na^+$, $K^+$, $Mg^{2+}$, $Ca^{2+}$, $NH_4^+$ cations and tetraalkylammonium cations.

The compounds meeting above formula (II) generally have particularly marked hydrophilic properties, which can be accounted for inter alia by the ability of the oxygen atoms of polyoxyethyleneglycol to form hydrogen bonds.

The presence of charge carrier functions on one or more of the $R^1$, $R^2$, $R^3$, $R^4$, $R^5$, $R^6$, $R^7$, $S^2$ and $S^1$ groups further increases the hydrophilic nature and generally allows the compounds to be water-soluble.

According to another embodiment of interest, in the formula (1) compounds according to the invention, the $S^1$ group (and optionally the $S^2$ group) comprises a phosphate group. The presence of this group imparts marked hydrophilic properties to this group, in particular by means of the charge carried by the phosphate group, which once again promotes the hydrophilic nature of the compound in water. According to this embodiment, the hydrophilic and fluorescent compound of the invention preferably meets following formula (III):

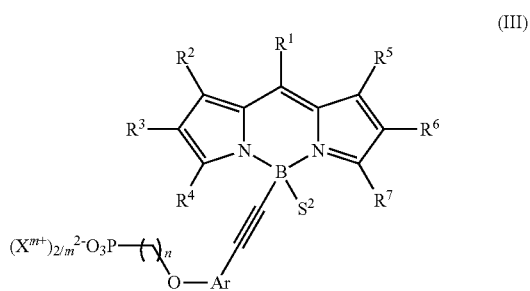

(III)

wherein:
$R^1$, $R^2$, $R^3$, $R^4$, $R^5$, $R^6$, $R^7$ and $S^2$ are such as defined above,
Ar is an arylene,
$X^{m+}$ is a cation (mono- or polyatomic, preferably of the aforementioned type) of valence m (this valence M typically being 1, 2, 3 or 4),
n' is an integer of 1, 2, 3 or 4.

According to another embodiment in the formula (1) compounds of the invention, the $S^1$ group (and optionally the $S^2$ group) comprises a zwitterionic group of ammonium sulphate or ammonium phosphate type. The presence of a group of this type, as $S^1$ group, generally imparts high hydrophilic properties to the compound, which is notably accounted for by the presence of the betaine form (association of the ammonium cation with the anionic group of phosphate or sulphate type). According to this embodiment, the hydrophilic and fluorescent compound of the invention preferably meets following formula (IV):

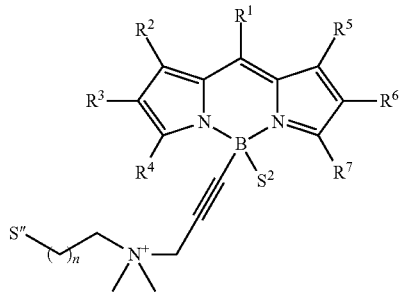

(IV)

wherein:
$R^1$, $R^2$, $R^3$, $R^4$, $R^5$, $R^6$, $R^7$ and $S^2$ are such as defined above,
n is 0, 1, 2, 3, 4 or 5,
S" is $-SO_3^-$ ou $-PO_3^{2-}(X^{m+})_{1/m}$
where $X^{m+}$ is a cation (mono- or polyatomic) of valence m (this valence M typically being 1, 2, 3 or 4)

Advantageously, in the compounds of the present invention, at least one of the groups $R^1$, $R^2$, $R^3$, $R^4$, $R^5$, $R^6$ or $R^7$ is a group carrying a polar functional group chosen from among the carboxylate, sulphonate, sulphate, phosphate, ammonium, hydroxyl, phosphonate and polyoxyethylene groups. The hydrophilic and fluorescent compounds according to this specific embodiment generally prove to be particularly hydrophilic, even water-soluble, which appears to be explained, at least in part, by the fact that they comprise at least one polar group on the dipyrromethene group in addition to the $S^1$ and/or $S^2$ polar groups on the boron. As pointed out above in the present description, the presence alone of a polar group on the dipyrromethene group is not in itself sufficient to ensure the sought-after hydrophilic property. Nonetheless, the work conducted by the inventors appears to indicate that in the presence of a $S^1$ (and optionally $S^2$) polar group on the boron ensuring hydrophilic properties, the polar group on the dipyrromethene group further increases the hydrophilic, even water-soluble nature.

In addition, in the formula (1) compounds of the invention $R^1$ is preferably a —Ar-L-Y group where:
Ar is an arylene,
L is a single bond; a straight or branched alkylene or a substituted straight or branched alkynylene,
Y is —Cl, —Br, —I, —COOH, —COOMe, —COOEt, —CONH—$CH_2$—$CH_2$—$NH_2$, —CONH—$CH_2$—COOEt, —CONH—$CH_2$—COOH, —CONH—$(CH_2)_q$—NCS, or else a group meeting one of the following formulas:

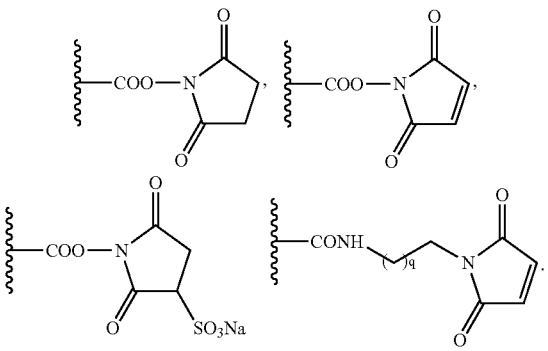

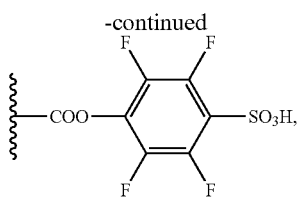

where q is 1, 2, 3, 4 or 5.

In formula —Ar-L-Y above, the Ar group is preferably a phenyl, and the L group is preferably a single bond or an alkynylene.

When $R^1$ is a —Ar-L-Y group, the compounds of the invention have the advantage of containing a function Y which may act as grafting function by reaction with the chemical function of a molecule, in particular a biological molecule. The fluorescent compound can then be particularly used as hydrophilic fluorescent marker or grafted onto solid hydrophilic substrates following techniques known per se, in particular from <<The Handbook A guide to fluorescence Probes and Labelling Technologies>> tenth edition, R. P. Haugland, Invitrogen 2005 and the references cited therein.

In the formula (1) compounds of the invention, according to one preferred embodiment:
  the groups $R^2$ and $R^5$ each independently are —H or -Me groups, and
  the groups $R^3$, $R^4$, $R^6$ and $R^7$ are independently chosen from —H, -Me, —C≡C—CH$_2$—N$^+$(Me)$_2$-(CH$_2$)$_n$—SO$_3^-$, —C≡C—Ar—R' and a group of formula:

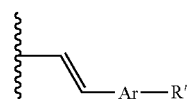

where:
  Ar is an arylene,
  R' is —OMe, —CH$_2$—PO$_3^{2-}$(X$^{m+}$)$_{2/m}$, or —C≡C—CH$_2$—R" where R" represents —O—(CH$_2$—CH$_2$—O)$_n$—CH$_3$, —O—(CH$_2$—CH$_2$—O)$_n$—CH$_2$—PO$_3^{2-}$(X$^{m+}$)$_{2/m}$, —O—(CH$_2$—CH$_2$—O)$_n$—CH$_2$—SO$_3^-$(X$^{m+}$)$_{1/m}$, —N$^+$(Me)$_2$-CH$_2$—(CH$_2$)$_n$—PO$_3^{2-}$(X$^{m+}$)$_{1/m}$ or —N$^+$(Me)$_2$-CH$_2$—(CH$_2$)$_n$—SO$_3^-$, in which:
    n is 1, 2, 3 or 4
    X$^{m+}$ is a cation (mono- or polyatomic) of valence m (this valence M typically being 1, 2 or 3).

More generally, in the compounds of the invention, the $R^3$, $R^4$, $R^6$ and $R^7$ groups are preferably chose from among —H, -Me and

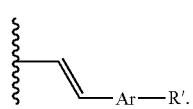

When $R^3$, $R^4$, $R^6$ and/or $R^7$ represent —C≡C—Ar—R' or

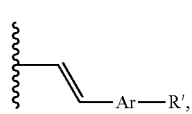

Ar preferably represents a phenyl or a thienyl.

According to one particularly preferred embodiment, in the compounds of the present invention:
  $R^1$ is an —Ar-L-Y group, where:
    Ar is an arylene,
    L is a single bond, a straight or branched alkylene or a substituted straight or branched alkynylene,
    Y represents —Cl, —Br, —I, —COOH, —COOMe, —COOEt, —CONH—CH$_2$—CH$_2$—NH$_2$, —CONH—CH$_2$—COOEt, —CONH—CH$_2$—COOH, —CONH—(CH$_2$)$_q$NCS, or else a group meeting one of the following formulas:

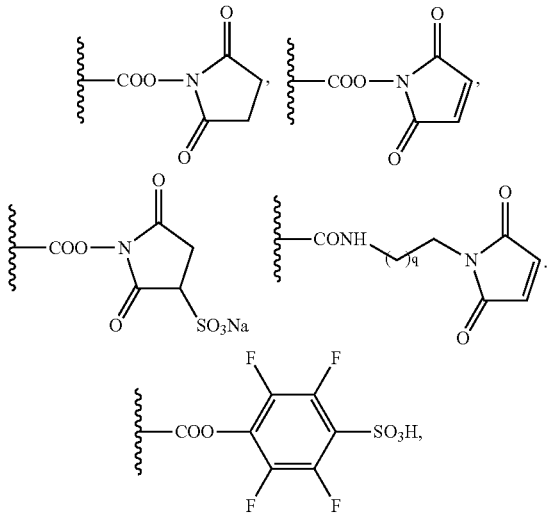

where q is 1, 2, 3, 4 or 5,
the groups $R^2$ and $R^5$ are chosen from among —H and -Me, and
the groups $R^3$, $R^4$, $R^6$ and $R^7$ are chosen from among —H, -Me, —C≡C—CH$_2$—N$^+$(Me)$_2$-(CH$_2$)$_n$—SO$_3^-$, —C≡C—Ar—R' and

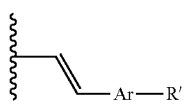

in which:
  Ar is an arylene,
  R' is —OMe, —CH$_2$—PO$_3^{2-}$(X$^{m+}$)$_{2/m}$, or —C≡C—CH$_2$—R" where R" represents —O—(CH$_2$—CH$_2$—O)$_n$—CH$_3$, —O—(CH$_2$—CH$_2$—O)$_n$—CH$_2$—PO$_3^{2-}$(X$^{m+}$)$_{2/m}$, —O—(CH$_2$—CH$_2$—O)$_n$—CH$_2$—SO$_3^-$(X$_{m+}$)$_{1/m}$, —N$^+$(Me)$_2$-CH$_2$—(CH$_2$)$_n$—PO$_3^{2-}$(X$^{m+}$)$_{1/m}$ or —N$^+$(Me)$_2$-CH$_2$—(CH$_2$)$_n$—SO$_3^-$, in which:
    n is 1, 2, 3 or 4
    X is a cation, and
    m is the valence of cation X.

According to one particular embodiment, the compounds of the invention are compounds of above-mentioned formula (1) where $R^2$ and $R^5$ are the same.

Typically (in particular for reasons of facilitating synthesis) the compounds of the invention are generally symmetric compounds, namely compounds in which:
  $R^2$ and $R^5$ are the same,
  $R^3$ and $R^6$ are the same, and
  $R^4$ and $R^7$ are the same.

Nevertheless, the present invention evidently extends to non-symmetric compounds which also have the properties and advantages inherent in all the compounds meeting general formula (I).

According to one preferred embodiment, the hydrophilic, fluorescent compounds of the invention may advantageously meet formula (Ia) below:

(Ia)

[Chemical structure of formula (Ia)]

wherein:
S' is such as defined,
Ar, L and Y are such as defined above,
n is 1, 2, 3 or 4,
$R^3$, $R^6$, $R^4$ and $R^7$ are chosen such that:
  $R^3$ and $R^6$ are the same and represent —H, and $R^4$ and $R^7$ are the same and represent -Me,
  $R^3$ and $R^6$ are the same and represent -Et, and $R^4$ and $R^7$ are the same and represent -Me,
  $R^3$ and $R^6$ are the same and represent —H, and $R^4$ and $R^7$ are the same and represent

[Chemical structure]

$R^3$ and $R^6$ are the same and represent —H, $R^4$ represents -Me and $R^7$ represents

[Chemical structure]

$R^3$ and $R^6$ are the same and represent —H, and $R^4$ and $R^7$ are the same and represent

[Chemical structure with —OMe]

$R^3$ and $R^4$ together form a divalent group —(CH$_2$)$_4$— and $R^6$ and $R^7$ together form a divalent group —(CH$_2$)$_4$—, or $R^3$ and $R^6$ are the same and represent —H, $R^4$ represents -Me and $R^7$ represents

[Chemical structure with thiophene]

which may or may not be substituted.

As non-limiting examples of well-adapted formula (Ia) compounds according to the invention, particular mention may be made of the compounds meeting formulas (Ia-1) to (Ia-20) below:

[Chemical structure]

Ia-1 $R^3 = R^6 = H$; $R^4 = R^7 = Me$
Ia-2 $R^3 = R^6 = Et$; $R^4 = R^7 = Me$
Ia-3 $R^3 = R^6 = H$; $R^4 = R^7 =$

[Chemical structure]

Ia-4 $R^3 = R^6 = H$; $R^4 = Me$; $R^7 =$

[Chemical structure]

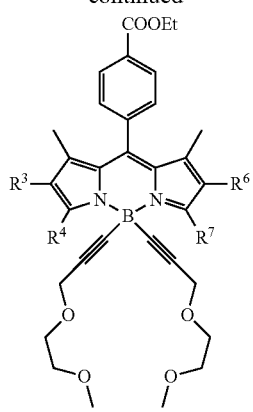
Ia-5 R³ = R⁶ = H; R⁴ = R⁷ = Me
Ia-6 R³ = R⁶ = Et; R⁴ = R⁷ = Me
Ia-7 R³ = R⁶ = H; R⁴ = R⁷ =
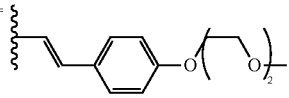
Ia-8 R³ = R⁶ = H; R⁴ = Me; R⁷ =
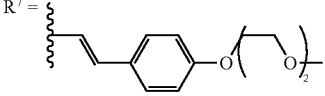
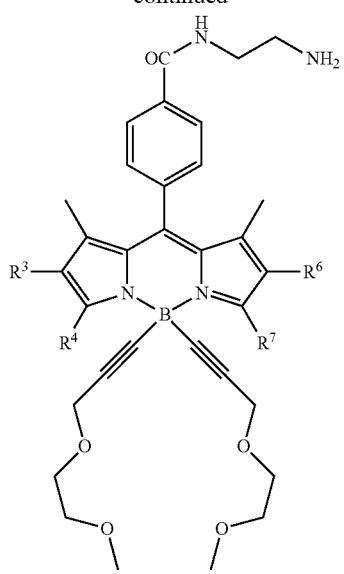
Ia-13 R³ = R⁶ = H; R⁴ = R⁷ = Me
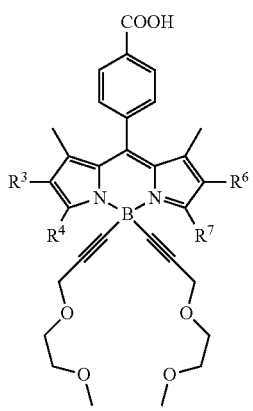
Ia-9 R³ = R⁶ = H; R⁴ = R⁷ = Me
Ia-10 R³ = R⁶ = Et; R⁴ = R⁷ = Me
Ia-11 R³ = R⁶ = H; R⁴ = R⁷ =
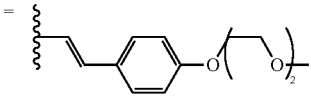
Ia-12 R³ = R⁶ = H; R⁴ = Me; R⁷ =
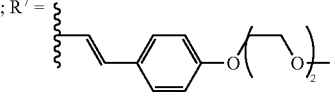
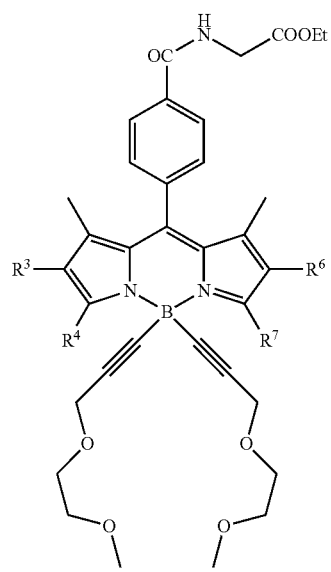
Ia-14 R³ = R⁶ = H; R⁴ = R⁷ = Me

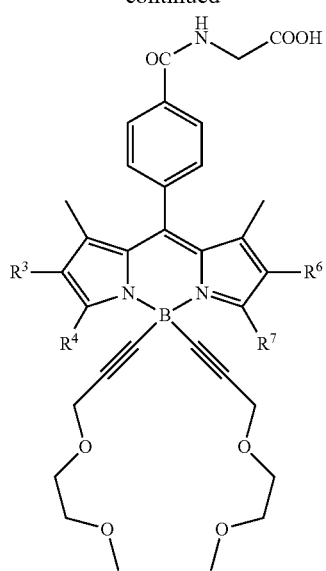
Ia-15 R³ = R⁶ = H; R⁴ = R⁷ = Me
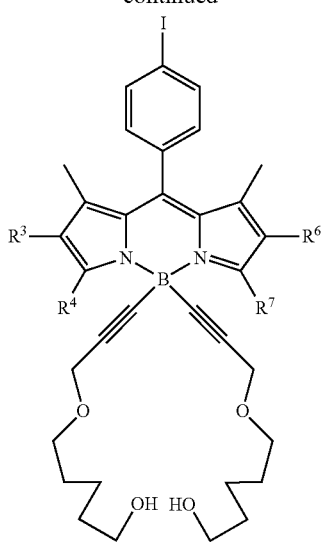
Ia-17 R³ = R⁶ = H; R⁴ = R⁷ = Me
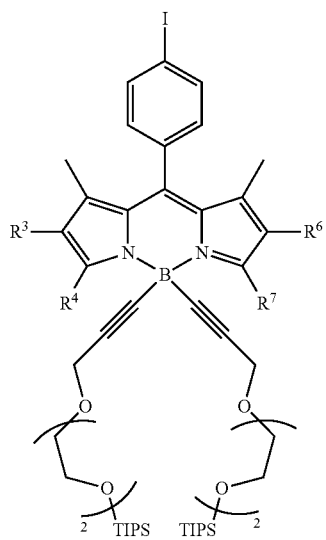
Ia-16 R³ = R⁶ = H; R⁴ = R⁷ = Me
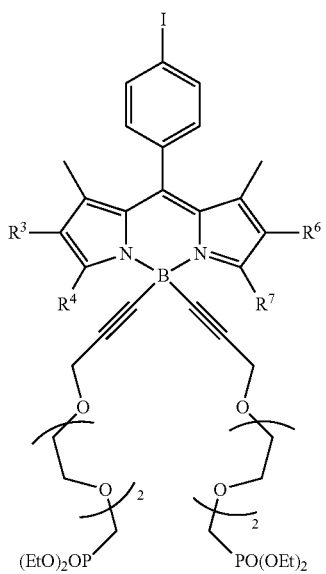
Ia-18 R³ = R⁶ = H; R⁴ = R⁷ = Me

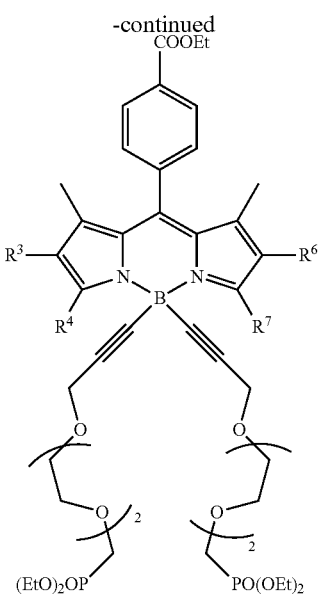

Ia-19 R³ = R⁶ = H; R⁴ = R⁷ = Me

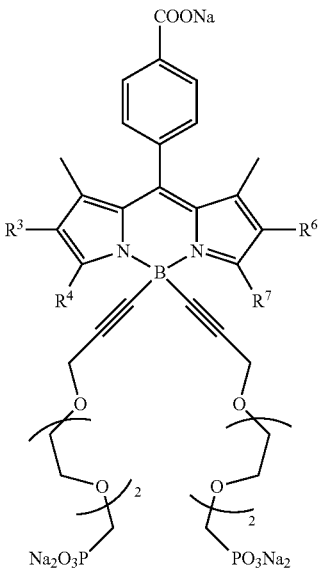

Ia-20 R³ = R⁶ = H; R⁴ = R⁷ = Me

Compounds Ia-1 to Ia-20 have the advantage of having similar optical properties to those of routinely used fluorophores:

- Ia-1, Ia-5, Ia-9, Ia-16 to Ia-20 have similar optical characteristics to fluorescein;
- Ia-2, Ia-6, Ia-10 have similar optical characteristics to Rhodamine 6G;
- Ia-4, Ia-8, Ia-12 have similar optical characteristics to TMR (tetramethyl rhodamine);
- Ia-3, Ia-7, Ia-11 have similar optical characteristics to TOTO-3 (1,2'-(4,4,7,7-tetramethyl-4,7-diazaundecamethylene)-bis-4-[3-methyl-2,3-dihydro-(benzo-1,3-thiazole)-2-propenylidene]-quinolinum tetraiodide).

According to one particular embodiment, the hydrophilic fluorescent compounds of the invention meet the following formula (Ic):

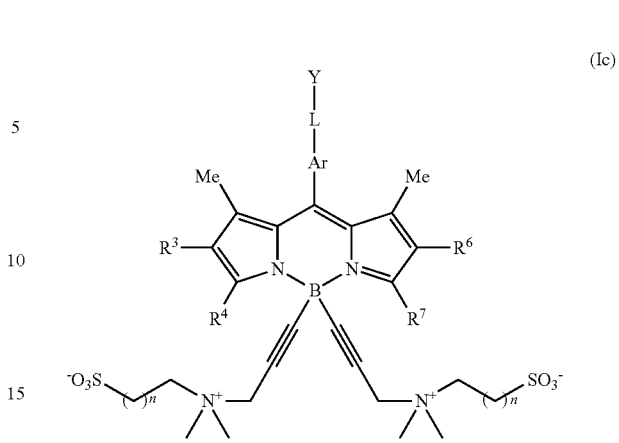

wherein:
Y, L and Ar are such as defined above,
R³, R⁶, R⁴ and R⁷ are such as defined above, and,
n is 2, 3 or 4.

As well-adapted formula (1c) compounds according to the present invention, particular mention may be made inter alia of the compounds of the following formulas (Ic-1), (Ic-2) and (Ic-3):

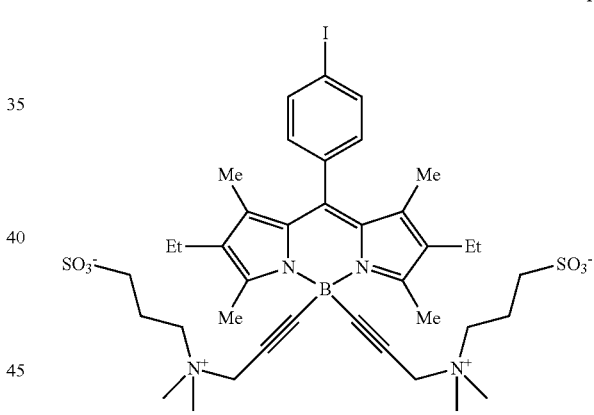

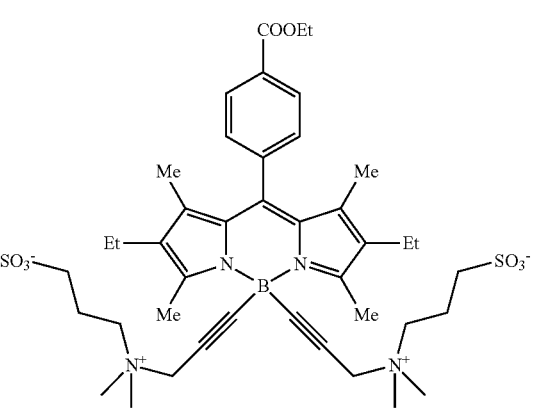

-continued
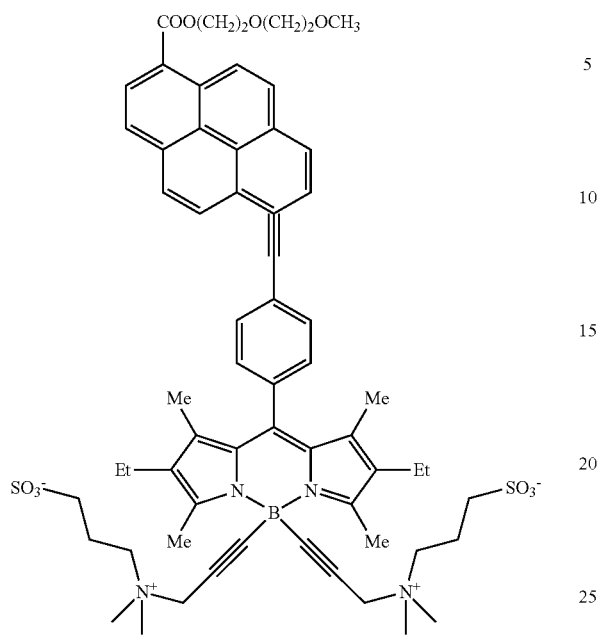
Ic-3
According to another embodiment, the hydrophilic fluorescent compounds of the invention meet following formula (Ie):
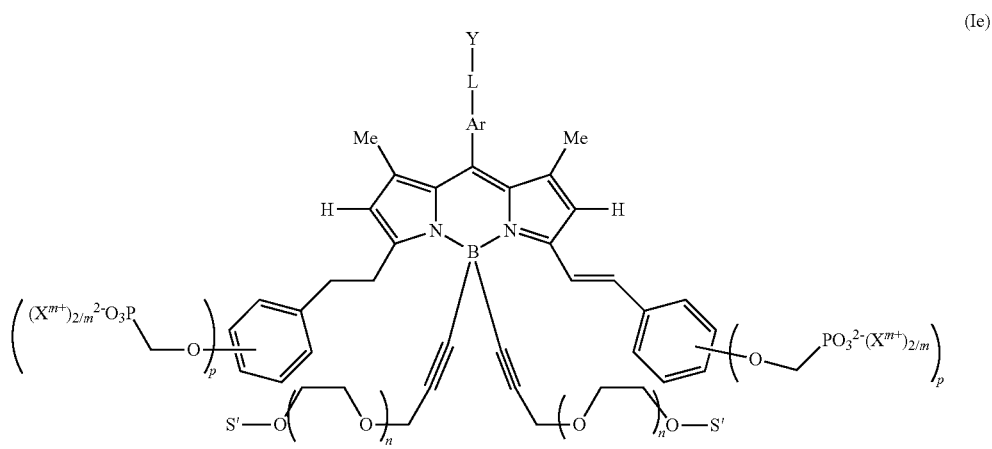
(Ie)
wherein:
Y, Ar and L are such as defined above, and
n is 1, 2, 3 or 4,
S' is such as defined above and preferably designates -Me,
X is a cation, and
m is the valence of cation X.
p is 1 or 2.

In one embodiment, the hydrophilic fluorescent compounds of the invention have the following formula (If):

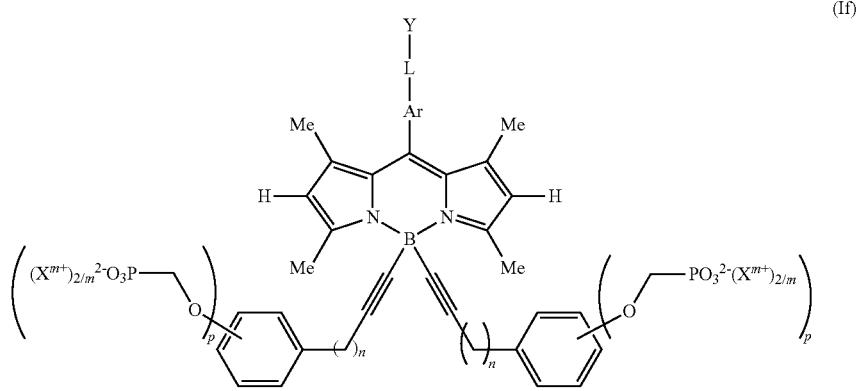

(If)

wherein:
Y, Ar and L are such as defined in claim 8, and
X is a cation,
n is 0, 1, 2, 3, or 4,
m is the valence of cation X, and
p is 1 or 2.

The compounds of the invention prove to be particularly useful as fluorescent marker in an aqueous medium. In one preferred embodiment, at least one of the groups $R^1$, $R^2$, $R^3$, $R^4$, $R^5$, $R^6$ and $R^7$ comprises a function allowing grafting on the molecule to be marked, in particular a Y function such as defined above. Preferably, the $R^1$ group of compounds used as fluorescent marker comprises a function allowing grafting on the molecule to be marked, in particular a Y function such as defined above.

Typically a hydrophilic, fluorescent compound according to the invention can be used for a marking method in an aqueous medium comprising a step for contacting a formula (1) compound in an aqueous medium, preferably in the solubilised state in said aqueous medium, with a molecule to be marked carrying a group able to react with one of the groups of the formula (I) compound, in particular the Y function.

The hydrophilic, fluorescent compounds of the invention can be used in a large number of applications including inter alia the following applications:
  marking molecules of biological interest:
    polypeptides and proteins
    oligonucleotides, DNA and RNA strand
    antibodies
    enzymes
  fluorescence microscopy
  flow cytometry
  fluoroimmunological assay.

The compounds may particularly be used for marking amino acids or nucleotides, which can then be used for synthesizing peptides or oligonucleotides respectively.

Also, by means of the increased chemical stability of the compounds according to the invention, compared with the compounds in which $S^1=S^2=F$, and the electrochemical properties thereof, the compounds of the invention can be used in optoelectronic systems such as OLEDs (organic light emitting diodes) and photovoltaic cells.

These techniques for marking, microscopy, fluorescence, flow cytometry and fluoroimmunological assay can be implemented with the compounds of the invention following the techniques reported in <<The Handbook A guide to fluorescence Probes and Labelling Technologies>> tenth edition, R. P. Haugland, Invitrogen 2005 and the references cited in this work.

These uses, according to another aspect, form one particular subject of the present invention.

The compounds of the invention can be synthesized using techniques known to persons skilled in the art.

As examples, routes of synthesis are described below for synthesizing specific compounds Ia-1 to Ia-20, which can be adapted for preparing other compounds meeting formula (I).

Compounds Ia-1 to Ia-4 can be obtained under action of Grignard methoxyethoxyethynyl in THF (tetrahydrofurane), typically at a temperature of around 60° C., for example following the protocol described in application PCT/WO 2006/087459A2 starting from Compounds 1-4 which were prepared following the literature of those skilled in the art. The iodine function can then be converted to carbonyl derivatives, for example in a carbon monoxide atmosphere in the presence of $[Pd(PPh_3)_2Cl_2]$ catalyst, in particular in a triethylamine/benzene mixture at 70° C. The choice of nucleophile used allows numerous functions to be directly obtained which can be used for coupling on a biological molecule or use in a protein synthesizer. With ethanol the ethyl esters Ia-5 to Ia-8 are obtained with very good yields, these esters are saponified to obtain the corresponding carboxylic acids Ia-9 to Ia-12 (Scheme 1). These compounds are highly hydrophilic. Ia-9, Ia-10 and Ia-12 have the advantage of being soluble in water at pH=7, in carboxylate form. The specific water-soluble compounds form one particular subject of the present invention. These carboxylic acids can be used directly for labelling, or spacers of amino acid type can be grafted using peptide coupling techniques.

Typically, the compounds can be synthesized following the ysnthesis route described in Scheme 1 below.

Scheme 1
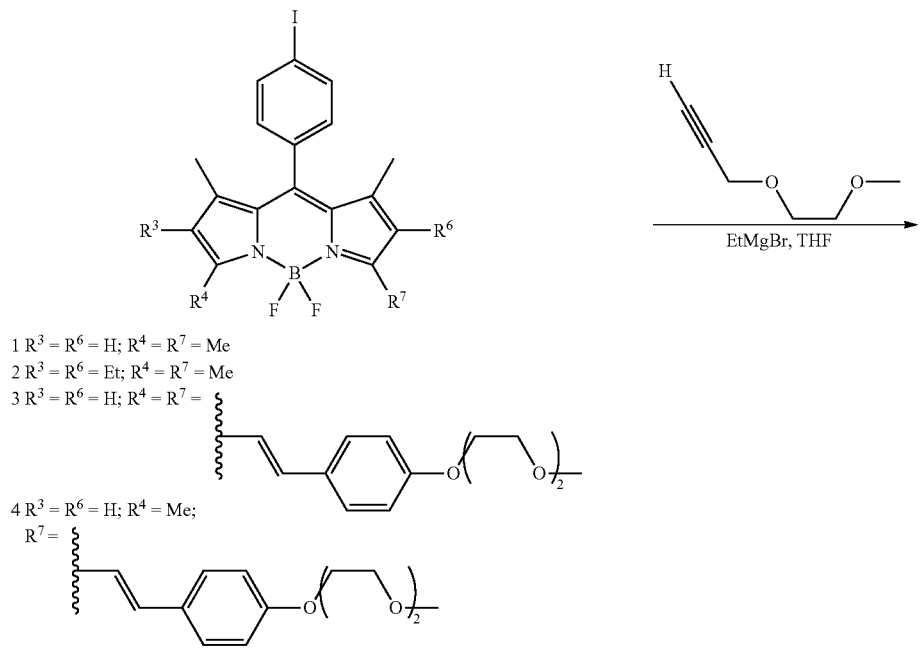
1 $R^3 = R^6 = H$; $R^4 = R^7 = Me$
2 $R^3 = R^6 = Et$; $R^4 = R^7 = Me$
3 $R^3 = R^6 = H$; $R^4 = R^7 = $
4 $R^3 = R^6 = H$; $R^4 = Me$;
$R^7 = $
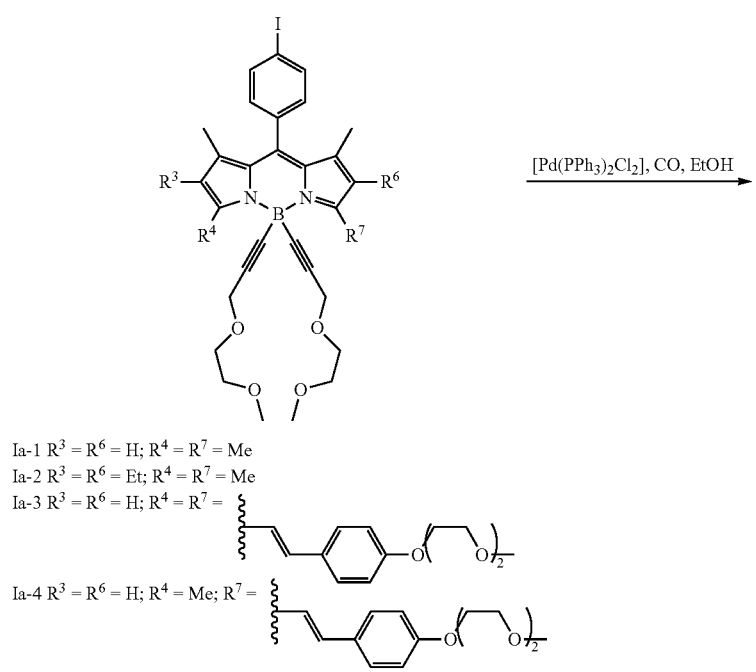
Ia-1 $R^3 = R^6 = H$; $R^4 = R^7 = Me$
Ia-2 $R^3 = R^6 = Et$; $R^4 = R^7 = Me$
Ia-3 $R^3 = R^6 = H$; $R^4 = R^7 = $
Ia-4 $R^3 = R^6 = H$; $R^4 = Me$; $R^7 = $ -continued

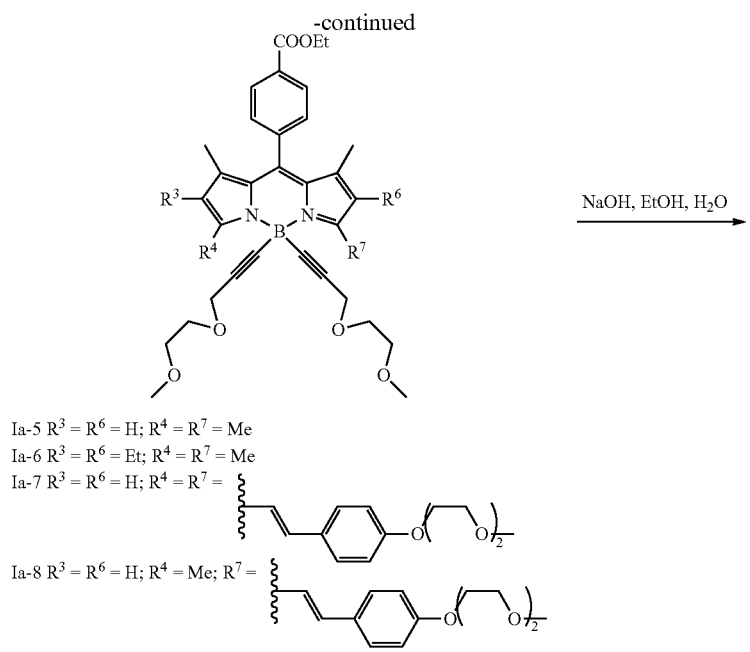

Ia-5 R³ = R⁶ = H; R⁴ = R⁷ = Me
Ia-6 R³ = R⁶ = Et; R⁴ = R⁷ = Me
Ia-7 R³ = R⁶ = H; R⁴ = R⁷ = [structure]
Ia-8 R³ = R⁶ = H; R⁴ = Me; R⁷ = [structure]

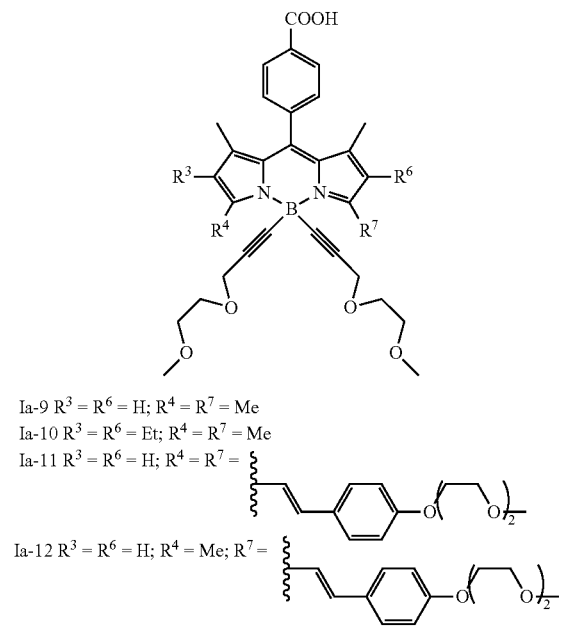

Ia-9 R³ = R⁶ = H; R⁴ = R⁷ = Me
Ia-10 R³ = R⁶ = Et; R⁴ = R⁷ = Me
Ia-11 R³ = R⁶ = H; R⁴ = R⁷ = [structure]
Ia-12 R³ = R⁶ = H; R⁴ = Me; R⁷ = [structure]

Using an aliphatic diamine in excess, compound Ia-13 can be obtained. A protected amino acid (e.g. glycine ethyl ester) can also be directly added to give Ia-14, whose corresponding carboxylic acid Ia-15 can be obtained by saponification (Scheme 2). Compound Ia-15 has the advantage of being water-soluble.

Typically, the compounds can be synthesized following the synthesis route described in Scheme 2 below.

Scheme 2

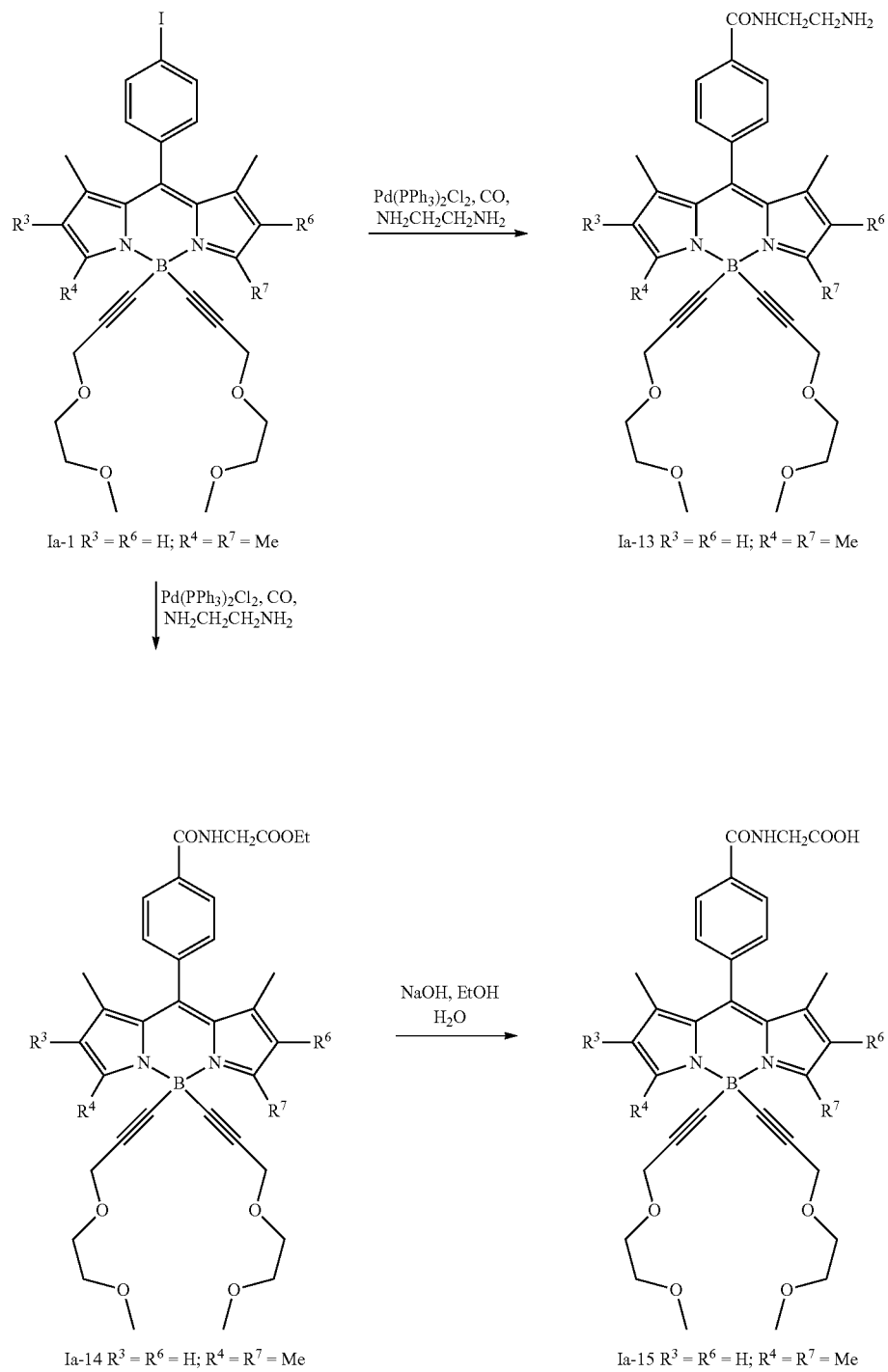

Compound Ia-16 can particularly be obtained through action of Grignard triisopropylsillyloxyethoxyethynyl, e.g. in THF at 60° C., in particular following the procedure described in PCT/WO 2006/087459A2 starting from Compound 1. The TIPS (triisopropylsilyl) protector group can then be removed in an acid medium e.g. with a 0.1M aqueous HCl solution. The dialcohol Ia-17 can then be deprotonated e.g. with potassium t-butoxide, and diethyl phosphonate triflate can be added. Compound Ia-18 can then be modified at meso position, carrying an aryl iodide. An ethyl ester can be synthesized by reaction with carbon monoxide, e.g. in the presence of ethanol, [Pd(PPh$_3$)$_2$Cl$_2$] catalyst in a triethylamine benzene mixture at around 70° C. Compound Ia-19 thus obtained can be saponified to give the targeted compound Ia-20 (Scheme 3).

Typically, the compounds can be synthesized following the synthesis route described in Scheme 3 below.

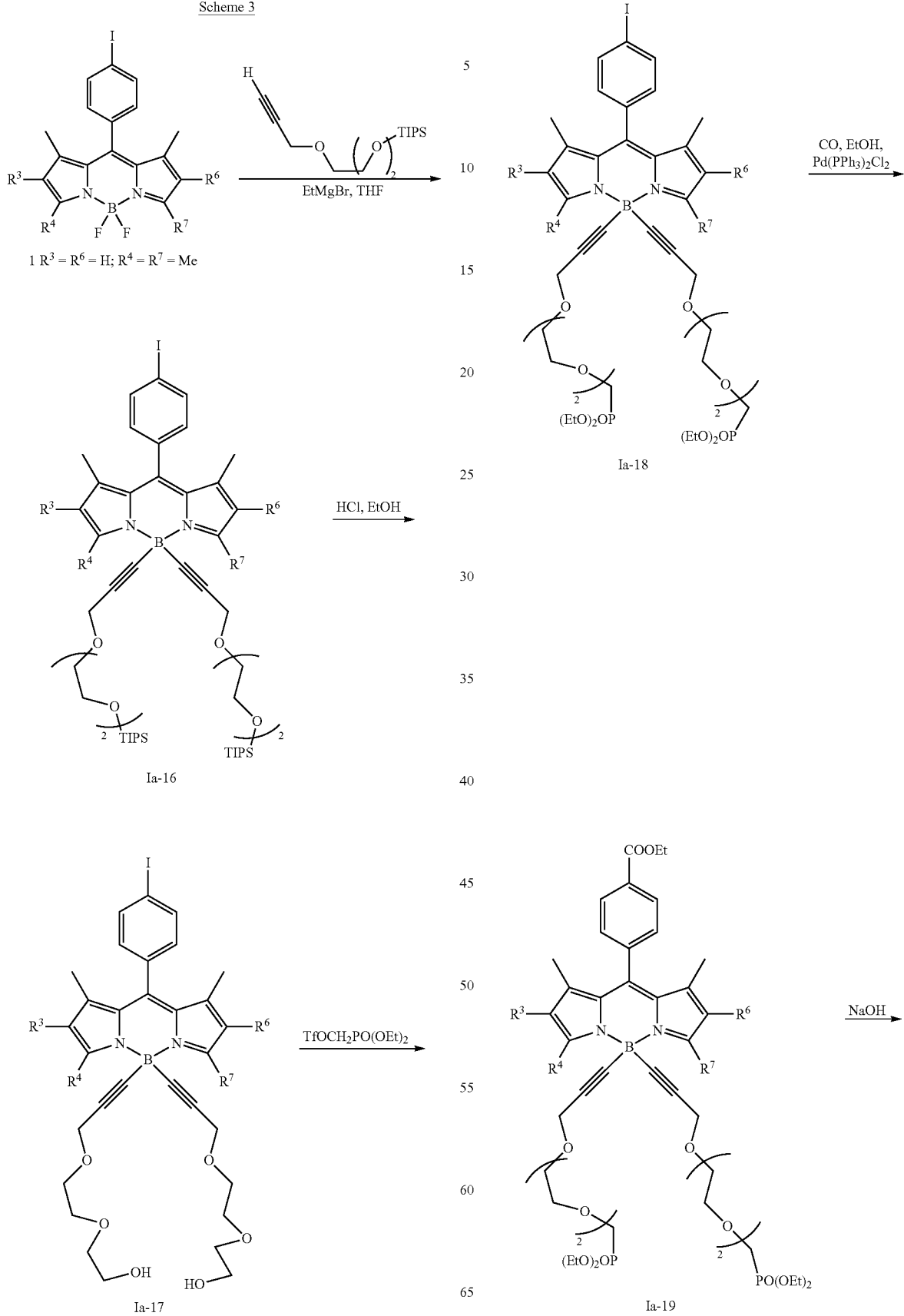
Scheme 3

29

-continued

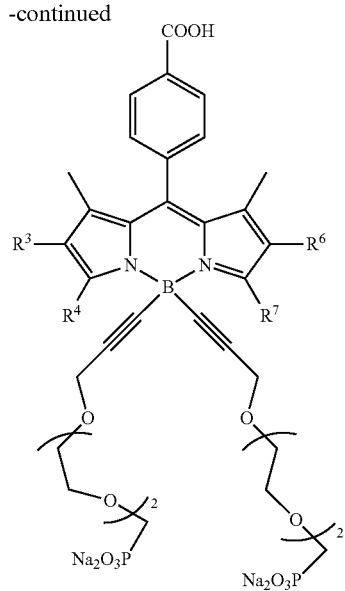

Ia-20

30

The compounds of the Ic family can be obtained by following the synthesis protocol described for Scheme 4. For example, compound 2a can react with Grignard dimethylamino-propyn, in particular in THF at around 60° C., to obtain the intermediate compound Ic-0. This compound can then be placed in the presence of propanesultone, e.g. in toluene, to give the compound Ic-1. Compound Ic-1 has the advantage of being water-soluble. The iodine function of compound Ic-1 can be used for example to add a carboxylic ester by carboalkoxylation reaction, in particular in the presence of a palladium catalyst to give compound Ic-2, the latter can readily be saponified by a skilled person to give the corresponding carboxylic acid. One group which can be used as additional chromophore (to form a dyade, i.e. a molecule composed of two fluorophores absorbing at different wavelengths and in which the high energy absorbing party transfers energy to the second which then emits light of lower energy) can also be added e.g. via coupling catalysed by palladium sub-liganded with a di-substituted pyrene carrying a true acetylene function, to give the fluorophore Ic-3. Similarly, the ester function can readily be saponified (Scheme 4).

Typically the compounds can be synthesized following the synthesis route described in Scheme 4 below.

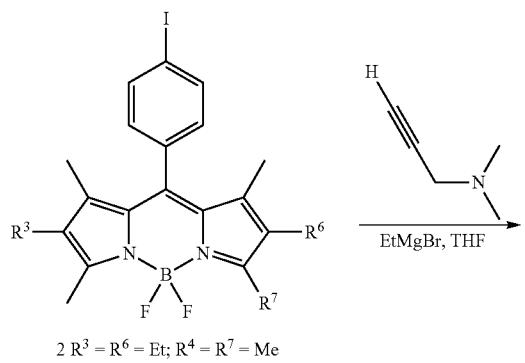

2 $R^3 = R^6 = Et; R^4 = R^7 = Me$

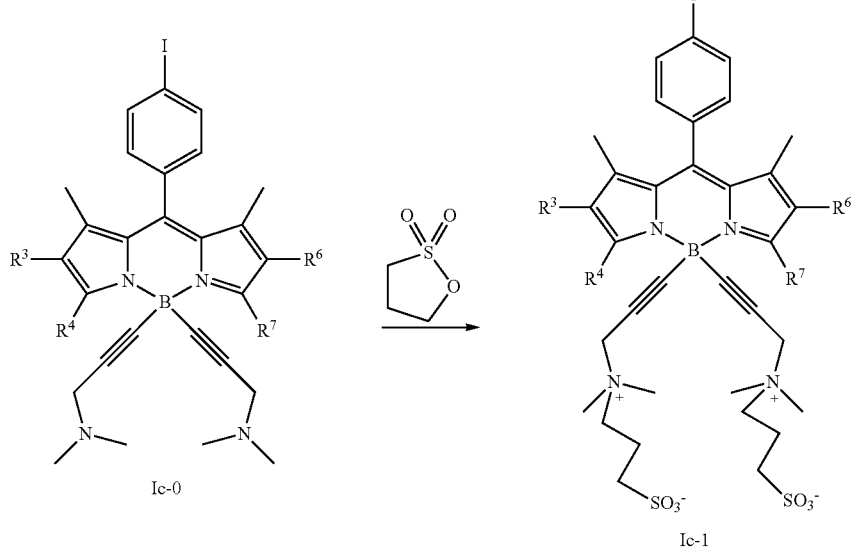

Ic-0

Ic-1

31    -continued    32
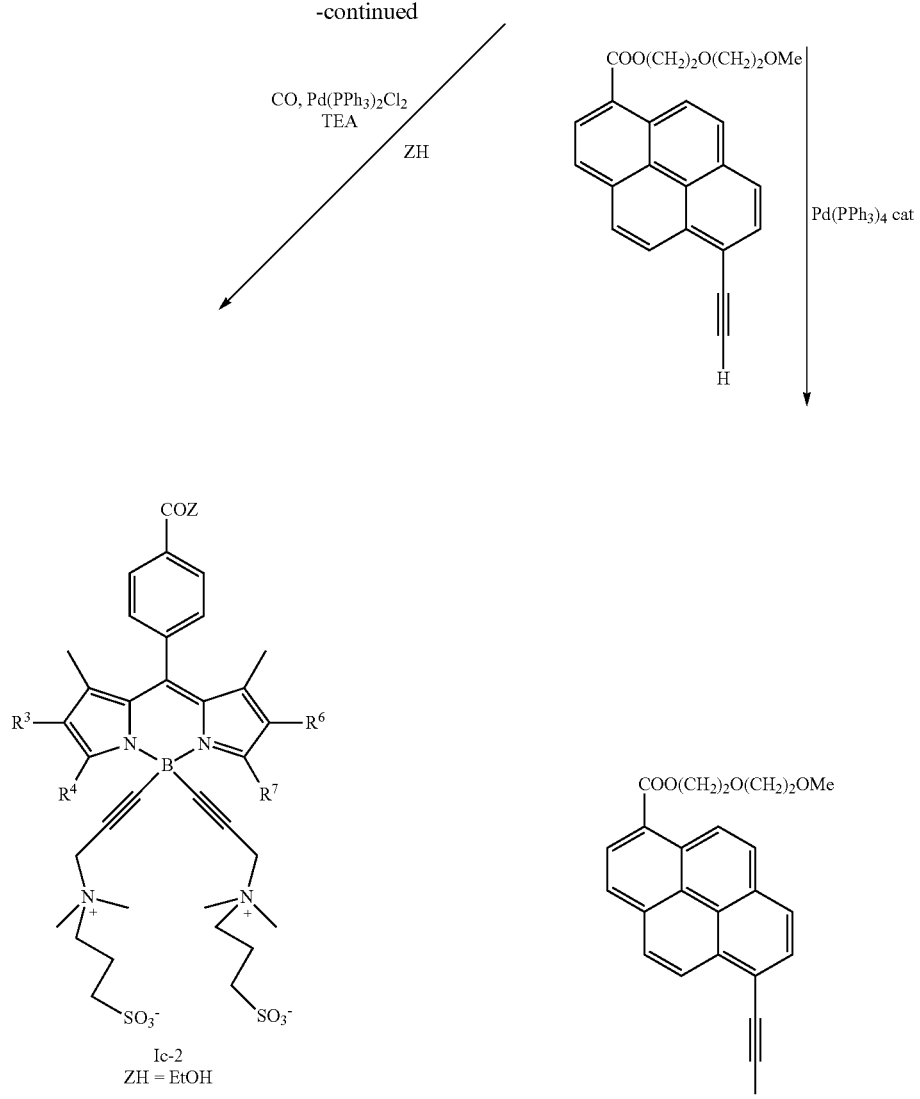
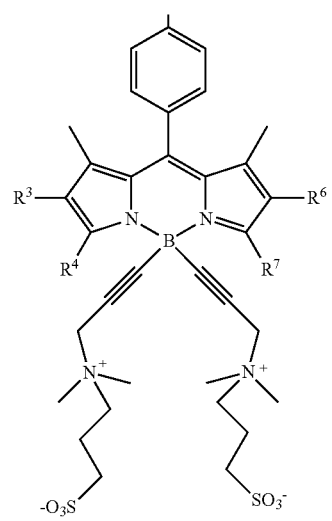

The specific water-soluble compounds Ia-9, Ia-10, Ia-12, Ia-15 and Ic-1 form a particular subject of the present invention.

EXAMPLES

The different hydrophilic, fluorescent compounds according to the invention were synthesized following the protocols described below.

Preparation of Compound Ia-1

Compound Ia-1 was prepared according to the following reaction scheme:

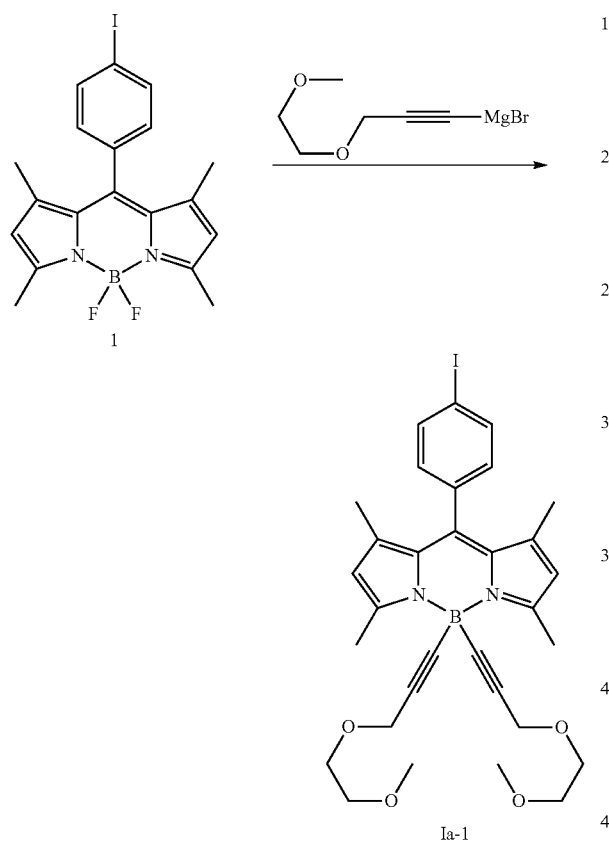

Ia-1

To a solution of 2,5-dioxaoct-7-yne (1.1 mL, 8.90 mmol) in anhydrous THF, at room temperature, ethylmagnesium bromide (1.0 M in THF, 8 ml) was added under argon. The mixture was stirred 2 h at 60° C., then left to cool at room temperature. The solution obtained was transferred by cannula to a solution of difluoroboradipyrromethene 1b (900 mg, 1.778 mmol) in anhydrous THF. The solution was left under stirring overnight at 60° C., after which water was added. This solution was extracted with dichloromethane. The organic phase was then washed with water (3×20 ml) then with NaCl-saturated solution (1×20 ml). After evaporation, the organic residue was purified by column chromatography on silica gel (Ethyl acetate/Petroleum ether, 10:90; 20:80; 30:70), and compound Ia-1 was obtained in orange powder form (1080 mg, 87%).

Characterization of Compound Ia-1

$^1$H NMR (CDCl$_3$ 300 MHz): 0.94 (t, 3H, $^3$J=7.55 Hz), 1.26 (s, 6H), 2.29 (q, 4H, $^3$J=7.55 Hz), 2.65 (s, 6H), 3.31 (s, 6H), 3.50 (m, 4H), 3.61 (m, 4H), 4.15 (s, 4H), 7.40 (AB sys, 4H, J$_{AB}$=8.55 Hz, u$_o$δ=226.42 Hz);

$^{13}$C NMR (CDCl$_3$, 300 MHz): δ=12.19, 14.09, 14.80, 17.44, 59.06, 59.82, 68.60, 71.88, 90.72, 94.35, 128.84, 130.66, 133.11, 136.07, 136.10, 138.21, 138.53, 154.

UV-Vis (CH$_2$Cl$_2$) λ nm (ε, M$^{-1}$ cm$^{-1}$)=501 (90000), 365 (4500), 325 (5300), 280 (8700);

Elementary analysis calculated for C$_{31}$H$_{36}$BIN$_2$O$_4$: C, 58.33; H, 5.68; N, 4.39. Found: C, 58.12; H, 5.41; N, 4.19.

Preparation of Compound Ia-2

Compound Ia-2 was prepared according to the following reaction scheme:

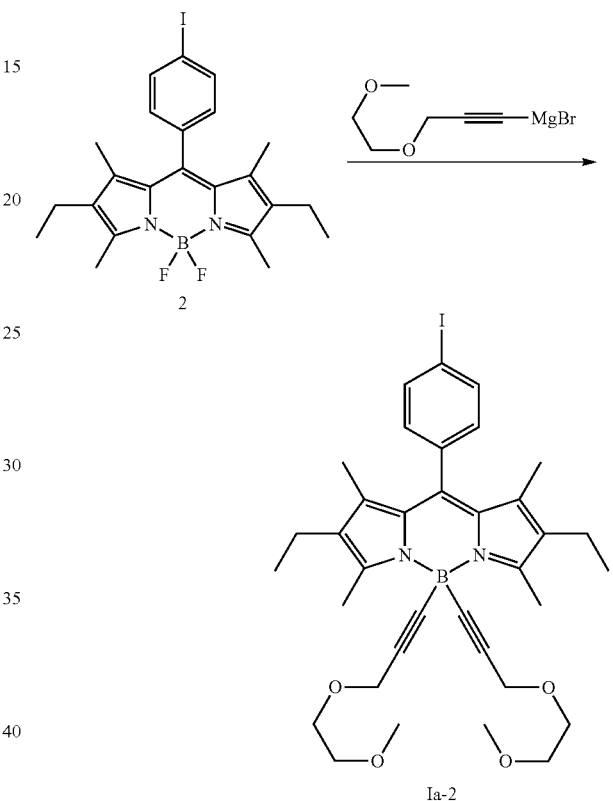

Ia-2

To a solution of 2,5-dioxaoct-7-yne (1.1 mL, 8.90 mmol) in anhydrous THF, at room temperature, ethylmagnesium bromide (1.0 M in THF, 8 ml) was added under argon. The mixture was stirred for 2 h at 60° C., then left to cool at room temperature. The solution obtained was transferred by cannula to a solution of difluoroboradiyrromethene 1b (900 mg, 1.778 mmol) in anhydrous THF. The solution was left under stirring overnight at 60° C., after which water was added. This solution was extracted with dichloromethane. The organic phase was next washed with water (3×20 ml) then with a NaCl-saturated solution (1×20 ml). After evaporation, the organic residue was purified by column chromatography on silica gel (Ethyl acetate/Petroleum ether, 10:90; 20:80; 30:70), and compound Ia-2 was obtained in orange powder form (1080 mg, 87%).

Characterization of Compound Ia-2

$^1$H NMR (CDCl$_3$ 300 MHz): 0.94 (t, 3H, $^3$J=7.55 Hz), 1.26 (s, 6H), 2.29 (q, 4H, $^3$J=7.55 Hz), 2.65 (s, 6H), 3.31 (s, 6H), 3.50 (m, 4H), 3.61 (m, 4H), 4.15 (s, 4H), 7.40 (AB sys, 4H, J$_{AB}$=8.55 Hz, u$_o$δ=226.42 Hz);

$^{13}$C NMR (CDCl$_3$, 300 MHz): δ=12.19, 14.09, 14.80, 17.44, 59.06, 59.82, 68.60, 71.88, 90.72, 94.35, 128.84, 130.66, 133.11, 136.07, 136.10, 138.21, 138.53, 154.

UV-Vis (CH$_2$Cl$_2$) λ nm (ε, M$^{-1}$ cm$^{-1}$)=522 (82000), 488 (20000), 381 (6400), 277 (6400);

Preparation of Compound Ia-3

Compound Ia-3 was prepared according to the following reaction scheme:

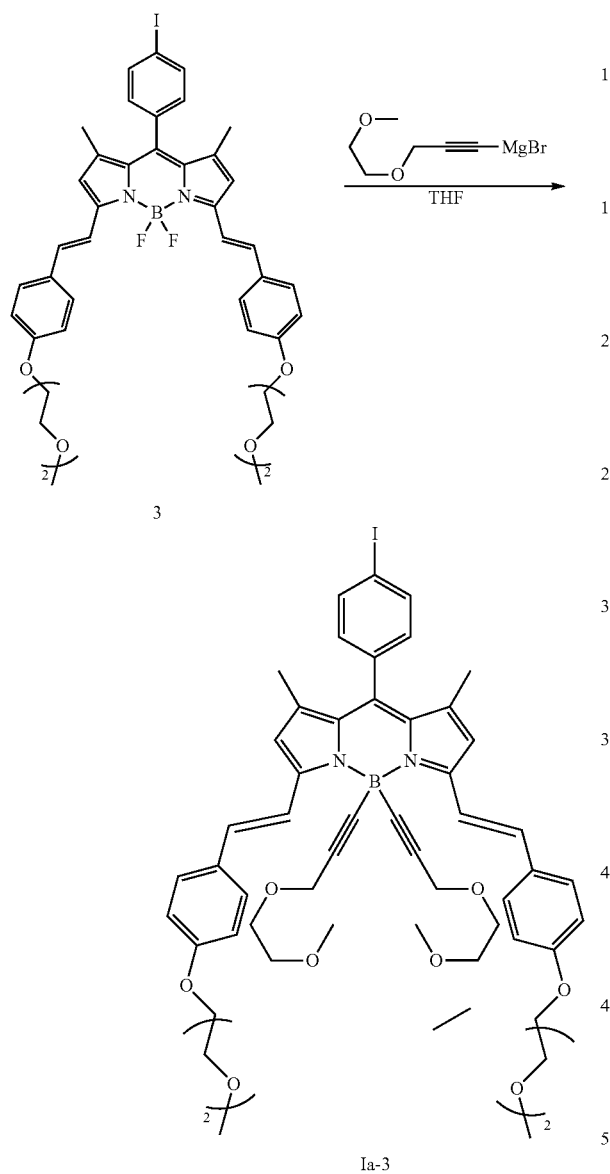

Ia-3

To a solution of 2,5-dioxaoct-7-yne (0.49 mL, 0.41 mmol) in anhydrous THF, at room temperature, ethylmagnesium bromide (1.0 M in THF, 3.7 ml) was added under argon. The mixture was stirred for 2 h at 60° C., then left to cool at room temperature. The solution obtained was transferred via cannula to a solution of difluoroboradipyrromethene 1c (670 mg, 0.816 mmol) in anhydrous THF. The solution was left under stirring overnight at 60° C., after which water was added. This solution was extracted with dichloromethane. The organic phase was next washed with water (3×20 ml) then with NaCl-saturated solution (1×20 ml). After evaporation, the organic residue was purified by column chromatography on silica gel (Ethyl acetate/Petroleum ether, 80:20; 100%), and compound Ia-3 was obtained in blue powder form (780 mg, 91%).

Characterization of Compound Ia-3

$^1$H NMR (CDCl$_3$ 300 MHz): 1.46 (s, 6H), 3.15 (m, 4H), 3.19 (s, 6H), 3.40 (s, 6H), 3.40 (s, 6H), 3.50 (m, 4H), 3.59 (m, 4H), 3.74 (m, 4H), 3.88 (m, 4H), 4.15 (s, 4H), 4.18 (m, 4H), 6.62 (s, 2H), 7.26 (AB sys, 8H, J$_{AB}$=8.65 Hz, uoδ=180.55 Hz), 7.11 (m, 4H), 7.82 (d, 2H), 8.05 (d, 2H).

$^{13}$C NMR (CDCl$_3$, 300 MHz): δ=15.21, 27.01, 58.86, 59.19, 59.50, 67.64, 68.26, 69.80, 70.91, 71.61, 72.07, 91.64, 94.62, 115.20, 118.15, 119.15, 128.89, 130.24, 130.80, 131.33, 134.16, 135.37, 136.82, 138.23, 140.04, 152.26, 159.62.

UV-Vis (CH$_2$Cl$_2$) λ nm (ε, M$^{-1}$ cm$^{-1}$)=646 (126600), 600 (43000), 371 (76500) 266 (8080);

Preparation of Compound Ia-4

Compound Ia-4 was prepared according to the following reaction scheme:

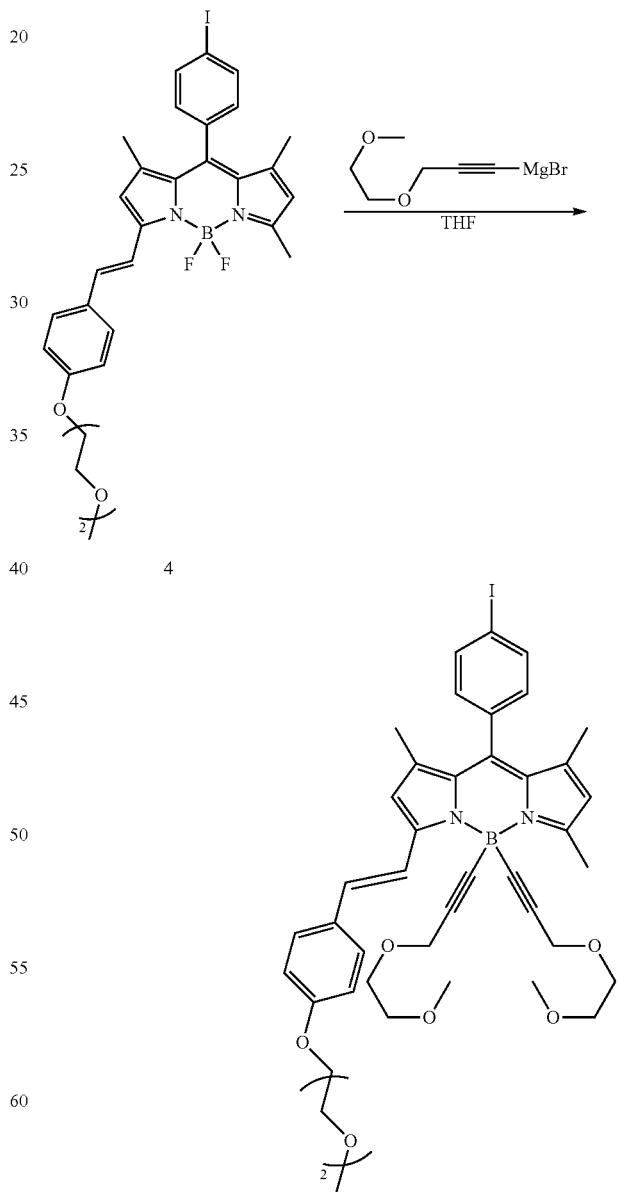

Ia-4

To a solution of 2,5-dioxaoct-7-yne (0.25 mL, 2.1 mmol) in anhydrous THF, at room temperature, ethylmagnesium bromide (1.0 M in THF, 1.90 ml) was added under argon. The mixture was stirred for 2 h at 60° C., then left to cool at room temperature. The solution obtained was transferred via cannula to a solution of difluoroboradipyrromethene 4 (273 mg, 0.418 mmol) in anhydrous THF. The solution was stirred overnight at 60° C., after which water was added. This solution was extracted with dichloromethane. The organic phase was next washed with water (3×20 ml) then with NaCl-saturated solution (1×20 ml). After evaporation, the organic residue was purified by column chromatography on silica gel (Ethyl acetate/Petroleum ether, 20:80; 40:60), and compound Ia-4 was obtained in the form of a purple powder (300 mg, 85%).

Characterization of Compound Ia-4

$^1$H NMR (CDCl$_3$ 300 MHz): 1.40 (s, 3H), 1.44 (s, 3H), 2.73 (s, 3H), 3.25 (s, 6H), 3.30 (m, 4H), 3.39 (s, 3H), 3.54 (m, 4H), 3.59 (m, 2H), 3.72 (m, 2H) 3.87 (m, 2H) 4.17 (s, 4H), 6.02 (s, 1H), 6.59 (s, 1H), 7.22 (AB sys, 4H, J$_{AB}$=8.65 Hz, u$_o$δ=179.98 Hz); 7.48 (AB sys, 4H, J$_{AB}$=8.28 Hz, u$_o$δ=223.73 Hz), 7.57 (AB sys, 2H, J$_{AB}$=16.18 Hz, u$_o$δ=296.87 Hz)

$^{13}$C NMR (CDCl$_3$, 300 MHz): δ=14.31, 14.99, 15.20, 16.36, 58.94, 59.20, 59.58, 67.63, 68.41, 69.79, 70.91, 71.69, 72.06, 91.40, 94.64, 115.13, 118.01, 119.16, 121.84, 128.72, 129.94, 130.17, 130.52, 130.68, 133.94, 135.27, 138.28, 138.61, 140.44, 140.66, 152.45, 155.40, 159.58.

UV-Vis (CH$_2$Cl$_2$) λ nm (ε, M$^{-1}$ cm$^{-1}$)=572 (93500), 533 (27600), 328 (47800)

Preparation of Compound Ia-5

Compound Ia-1 was prepared according to the following reaction scheme:

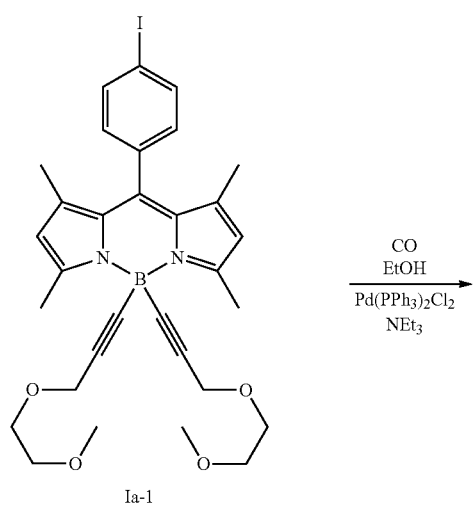

Ia-1

CO
EtOH
Pd(PPh$_3$)$_2$Cl$_2$
NEt$_3$

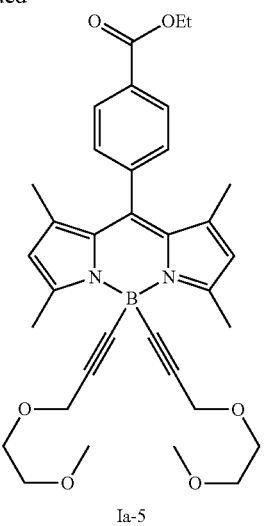

Ia-5

To a solution of compound Ia-1 (235 mg, 0.37 mmol) in 15 mL benzene were added 1 mL ethanol (17.2 mmol), 44 mg bis(triphenylphosphine) palladium bis-chloride (0.07 mmol) and 5 mL triethylamine. The solution was left under stirring at 70° C. overnight with carbon monoxide <<bubbling>>. The reaction mixture was extracted with dichloromethane and washed with water (3×20 mL). The organic phase was dried with hydrophilic cotton and evaporated. The residue was purified by column chromatography on silica gel (CH$_2$Cl$_2$/MeOH 99:1 or AcOEt/Petroleum ether 40:60) to yield compound Ia-5 in orange powder form (210 mg, 97%).

Characterization of Compound Ia-5

$^1$H NMR (CDCl$_3$, 400 MHz): δ=1.33 (s, 6H), 1.42 (t, 3H, $^3$J=7.0 Hz), 2.71 (s, 6H), 3.35 (s, 6H), 3.53 (m, 4H), 3.64 (m, 4H), 4.19 (s, 4H), 4.40 (q, 2H, $^3$J=7.0 Hz), 6.00 (s, 2H), 7.78 (AB sys, 4H, J$_{AB}$=8.5 Hz, v$_o$δ=300.4 Hz);

$^{13}$C {$^1$H} NMR (CDCl$_3$, 100 MHz): δ=14.4, 14.8, 16.1, 59.0, 59.7, 61.4, 68.4, 68.6, 71.8, 90.9, 121.8, 128.6, 129.1, 130.3, 131.0, 140.3, 140.3, 140.9, 155.6, 166.1;

$^{11}$B NMR (CDCl$_3$, 128.4 MHz): δ=−10.2 (s);

UV-Vis (CH$_2$Cl$_2$) λ nm (ε, M$^{-1}$ cm$^{-1}$)=500 (90000), 366 (4900), 308 (7700);

FAB$^+$ m/z: 585.2 ([M+H]$^+$, 100);

Elementary analysis calculated for C$_{34}$H$_{41}$BN$_2$O$_6$: C, 69.86; H, 7.07; N, 4.79. Found: C, 69.77; H, 7.04; N, 4.59.

Preparation of Compound Ia-6

Compound Ia-6 was prepared according to the following reaction scheme:

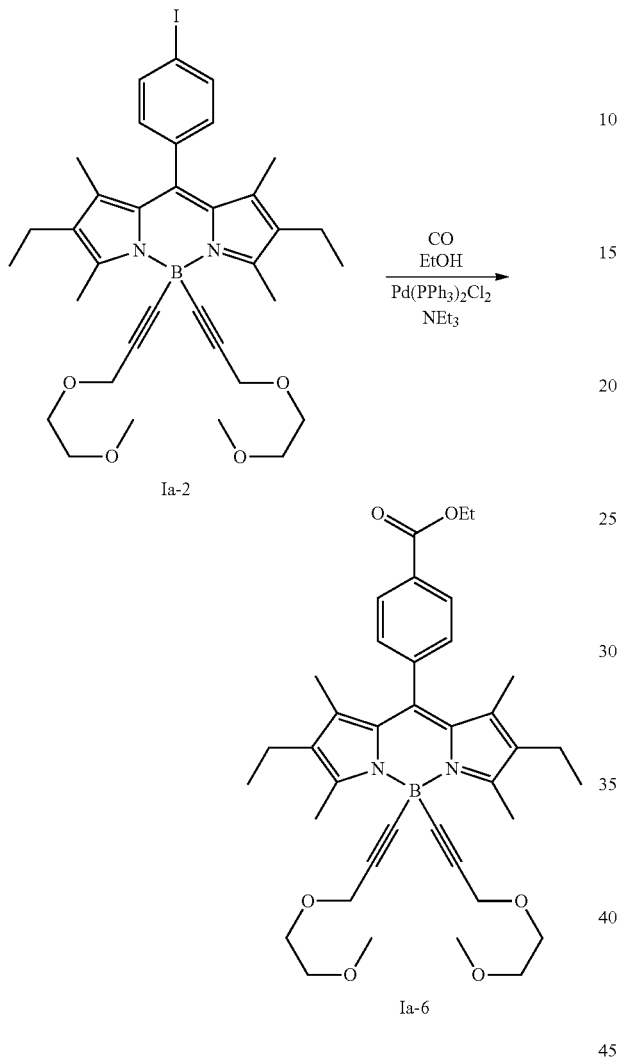

To a solution of compound 2b (980 mg, 1.41 mmol) in 50 mL benzene were added 3 mL ethanol (17.2 mmol), 240 mg bis(triphenylphosphine) palladium bis-chloride (0.07 mmol) and 15 mL triethylamine. The solution was stirred at 70° C. overnight with carbon monoxide <<bubbling>>. The reaction mixture was extracted with dichloromethane and washed with water (3×20 mL). The organic phase was dried on hydrophilic cotton and evaporated. The residue was purified by column chromatography on silica gel (AcOEt/Petroleum ether 20:80; 40:60) to yield compound Ia-6 in orange powder form (895 mg, quantitative).

Characterization of Compound Ia-6

$^1$H NMR (CDCl$_3$ 300 MHz): 0.97 (t, 6H, $^3$J=7.40 Hz), 1.23 (s, 6H), 1.43 (t, 3H, $^3$J=7.10 Hz), 2.31 (q, 4H, $^3$J=7.40 Hz) 2.69 (s, 6H), 3.35 (s, 6H), 3.53 (m, 4H), 3.65 (m, 4H), 4.19 (s, 4H), 4.43 (q, 2H, $^3$J=7.10 Hz), 7.78 (AB sys, 4H, J$_{AB}$=8.19 Hz, uoδ=223.07 Hz);

$^{13}$C NMR (CDCl$_3$, 300 MHz): δ=12.03, 14.07, 14.41, 14.76, 17.40, 29.78, 59.02, 59.79, 61.37, 68.57, 71.85, 90.67, 128.60, 128.95, 130.19, 130.81, 133.11, 136.02, 138.77, 141.27, 154.05, 166.28.

$^{11}$B NMR (CDCl$_3$, 128.4 MHz): δ=−10.2 (s);

UV-Vis (CH$_2$Cl$_2$) λ nm (ε, M$^{-1}$ cm$^{-1}$)=522 (80000), 488 (20000), 381 (6400), 277 (6400);

Preparation of Compound Ia-7

Compound Ia-2 was prepared according to the following reaction scheme:

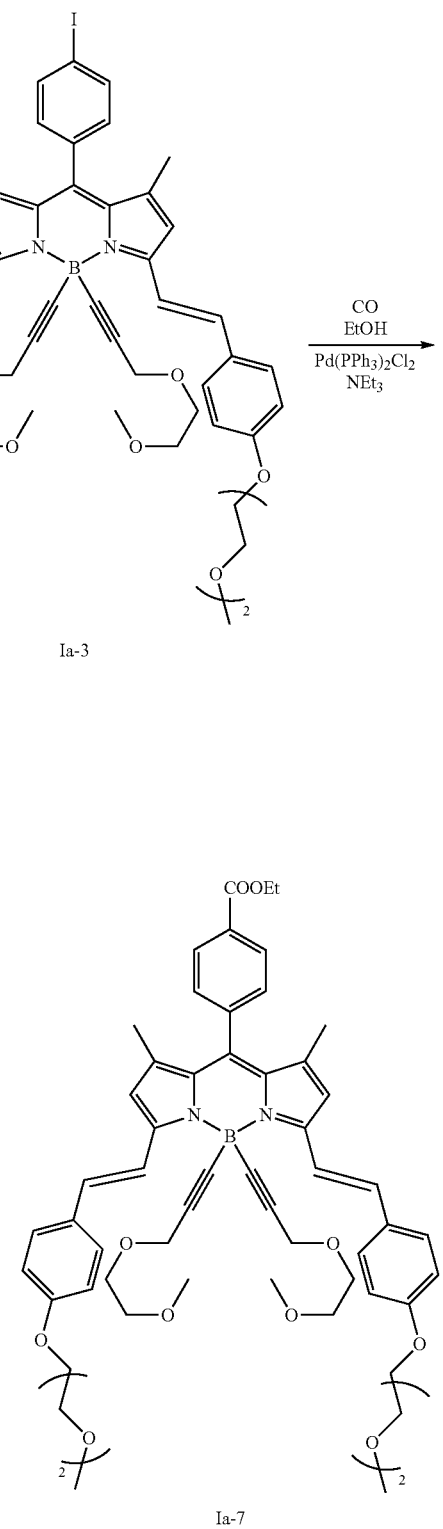

To a solution of compound 2c (100 mg, 0.095 mmol) in 25 mL benzene were added 1 mL ethanol (17.2 mmol), 24 mg bis(triphenylphosphine) palladium bis-chloride (0.035 mmol) and 5 mL de triethylamine. The solution was stirred at 70° C. overnight with carbon monoxide <<bubbling>>. The reaction mixture was extracted with dichloromethane and washed with water (3×10 mL). The organic phase was dried on hydrophilic cotton and evaporated. The residue was purified by column chromatography on silica gel (AcOEt/Petroleum ether 80:20; 100%) to give compound Ia-7 in the form of a blue powder (88 mg, 92%).

Characterization of Compound Ia-7

$^1$H NMR (CDCl$_3$ 200 MHz): 1.40 (s, 6H), 1.44 (t, 3H, $^3$J=10.5 Hz) 3.15 (m, 4H), 3.19 (s, 6H), 3.41 (s, 6H), 3.50 (m, 4H), 3.59 (m, 4H), 3.74 (m, 4H), 3.88 (m, 4H), 4.15 (s, 4H), 4.18 (m, 4H), 4.41 (q, 2H, $^3$J=10.5 Hz), 6.62 (s, 2H), 7.27 (AB sys, 8H, J$_{AB}$=8.73 Hz, u$_o$δ=120.73 Hz), 7.60 (AB sys, 4H, J$_{AB}$=16.26 Hz, u$_o$δ=192.63 Hz) 7.83 (AB sys, 4H, J$_{AB}$=8.34 Hz, u$_o$δ=141.89 Hz).

UV-Vis (CH$_2$Cl$_2$) λ nm (ε, M$^{-1}$ cm$^{-1}$)=647 (121000), 373 (72800),

Preparation of Compound Ia-8

Compound Ia-8 was prepared according to the following reaction scheme:

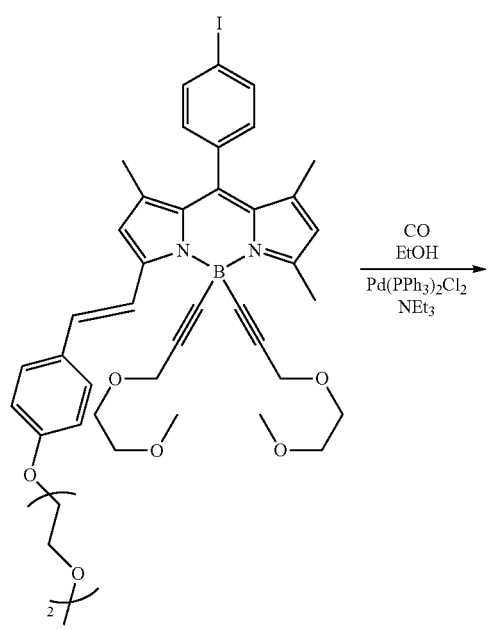

Ia-4

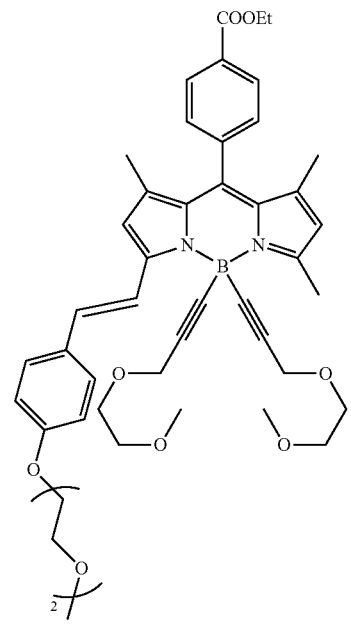

Ia-8

To a solution of compound Ia-4 (100 mg, 0.118 mmol) in 25 mL benzene were added 2 mL ethanol (XXX mmol), 24 mg bis(triphenylphosphine) palladium bis-chloride (0.07 mmol) and 5 mL triethylamine. The solution was stirred at 70° C. overnight with carbon monoxide <<bubbling>>. The reaction mixture was extracted with dichloromethane and washed with water (3×10 mL). The organic phase was dried on hydrophilic cotton and evaporated. The residue was purified by column chromatography on silica gel (AcOEt/Petroleum ether 20:80; 40:60) to give compound Ia-8 in the form of a purple powder (82 mg, 88%).

Characterization of Compound Ia-8

$^1$H NMR (CDCl$_3$ 300 MHz): 1.35 (s, 3H), 1.38 (s, 3H), 1.43 (t, 3H, $^3$J=7.15 Hz) 2.74 (s, 3H), 3.25 (s, 6H), 3.31 (m, 4H), 3.39 (s, 3H), 3.54 (m, 6H), 3.72 (m, 2H), 3.87 (m, 2H), 4.18 (m, 4H), 4.43 (q, 2H, $^3$J=7 Hz), 6.02 (s, 1H), 6.59 (s, 1H), 7.22 (AB sys, 4H, J$_{AB}$=8.67 Hz, u$_o$δ=180.18 Hz); 7.58 (AB sys, 2H, J$_{AB}$=16.29 Hz, u$_o$δ=297.72 Hz), 7.85 (AB sys, 4H, J$_{AB}$=7.99 Hz, u$_o$δ=226.28 Hz)

Preparation of Compound Ia-9

Compound Ia-9 was prepared according to the following reaction scheme:

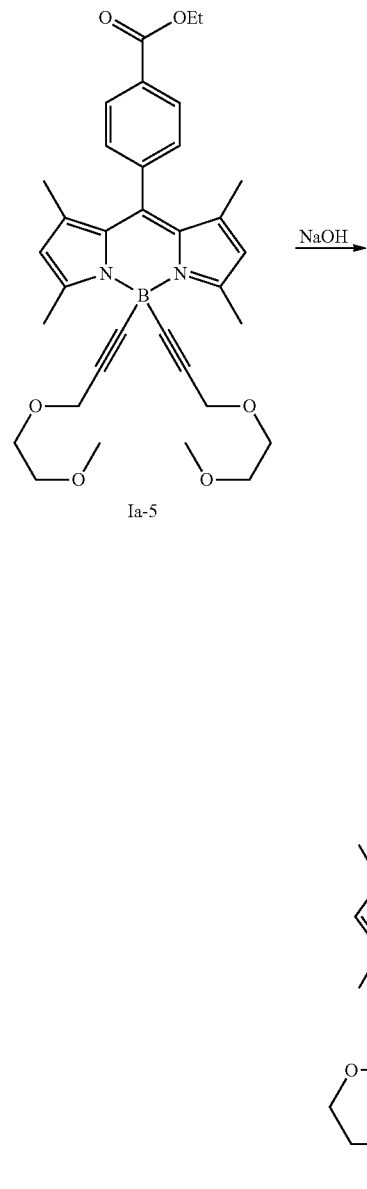

To a solution of compound 3a (210 mg, 0.36 mmol) in 20 mL ethanol, 215 mg of sodium hydroxide (5.39 mmol) were added. The solution was stirred 3 hours at room temperature. 30-40 mL ethyl acetate was added. The organic phase was extracted with water (3×20 mL). The aqueous phases were combined and acidified with 1 M aqueous HCl solution to pH 1-2. The aqueous phase was extracted with dichloromethane. The organic phase was dried on hydrophilic cotton then evaporated to dryness to yield compound 5a in the form of an orange powder (190 mg, 95%).

Characterization of compound II-5a

UV-Vis (CH$_2$Cl$_2$) λ nm (ε, M$^{-1}$ cm$^{-1}$)=501 (72800), 366 (4000), 307 (6400);

UV-Vis (PBS buffer) λ nm (ε, M$^{-1}$ cm$^{-1}$)=494 (71500), 364 (3900), 307 (4900);

Preparation of Compound Ia-10

Compound Ia-10 was prepared according to the following reaction scheme:

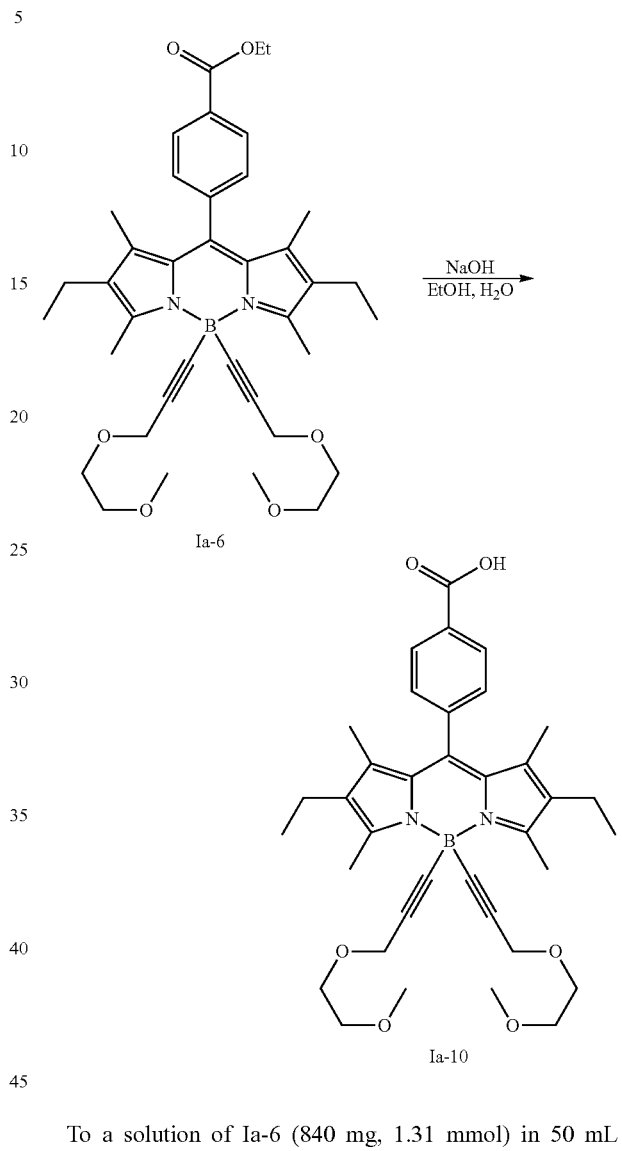

To a solution of Ia-6 (840 mg, 1.31 mmol) in 50 mL ethanol, 2.10 g sodium hydroxide (0.525 mol) was added. The solution was stirred overnight at room temperature. 30-40 mL ethyl acetate was added. The organic phase was extracted with water (3×20 mL). The aqueous phases were combined and acidified with 1M aqueous HCl solution to pH 1-2. The aqueous phase was extracted with dichloromethane. The organic phase was dried on hydrophilic cotton then evaporated to dryness to give compound Ia-10 in the form of an orange powder (778 mg, 97%).

$^1$H NMR (CDCl$_3$, 300 MHz): 0.97 (t, 6H, $^3$J=7.35 Hz), 1.23 (s, 6H), 2.31 (q, 4H, $^3$J=7.35 Hz) 2.69 (s, 6H), 3.35 (s, 6H), 3.53 (m, 4H), 3.65 (m, 4H), 4.19 (s, 4H), 7.78 (AB sys, 4H, J$_{AB}$=8.19 Hz, u$_o$δ=223.07 Hz);

UV-Vis (PBS buffer) λ nm (ε, M$^{-1}$ cm$^{-1}$)=517 (65000), 379 (3600), 320 (5000);

Preparation of Compound Ia-11

Compound Ia-11 was prepared according to the following reaction scheme:

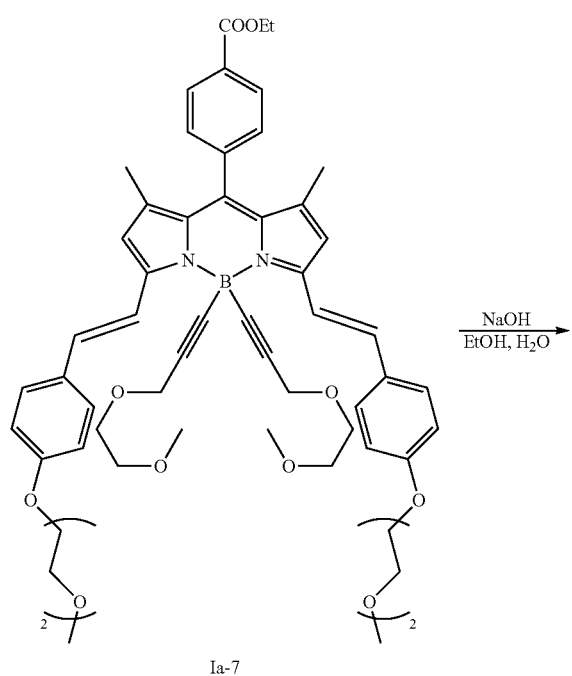

Ia-7

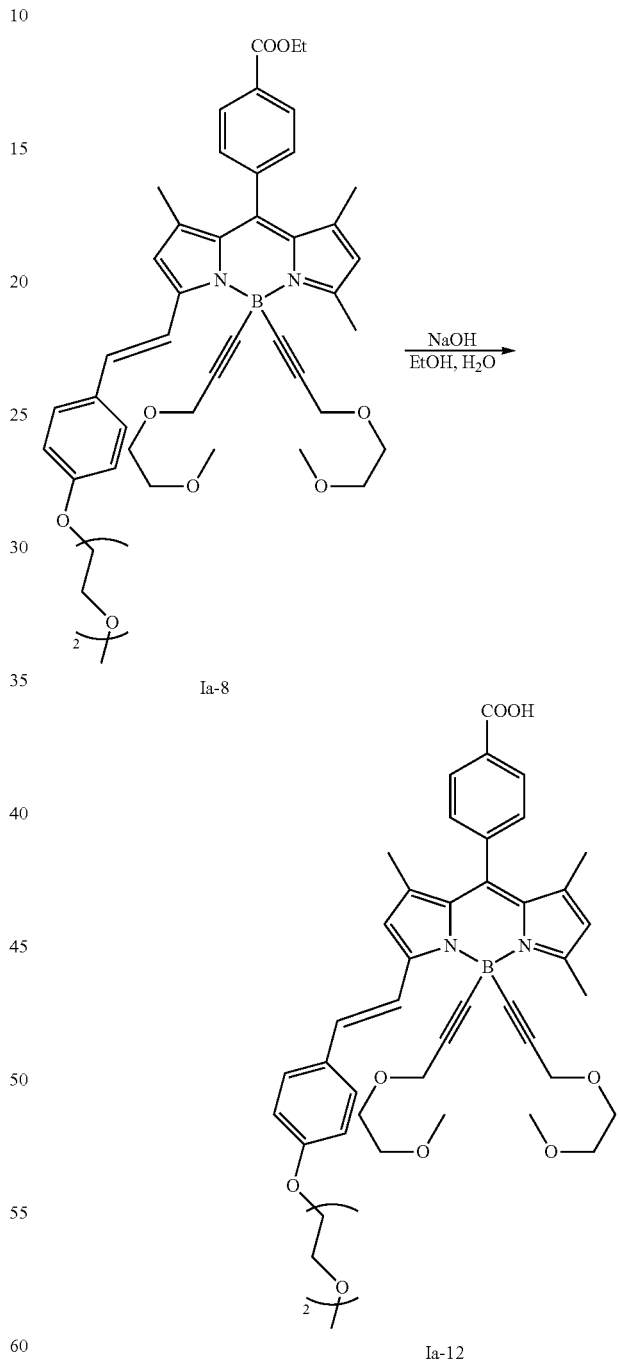

Ia-8

Ia-11

7.28 (AB sys, 8H, $J_{AB}$=8.6 Hz, $u_o\delta$=120.59 Hz), 7.61 (AB sys, 4H, $J_{AB}$=16.1 Hz, $u_o\delta$=191.44 Hz) 7.88 (AB sys, 4H, $J_{AB}$=8.19 Hz, $u_o\delta$=144.73 Hz).

UV-Vis ($CH_2Cl_2$) λ nm (ε, $M^{-1}$ $cm^{-1}$)=647 (118000), 373 (67800),

Preparation of Compound Ia-12

Compound Ia-12 was prepared according to the following reaction scheme:

Ia-12

To a solution of compound Ia-7 (80 mg, 0.080 mmol) in 20 mL ethanol was added 130 mg sodium hydroxide (3.22 mmol). The solution was stirred overnight at room temperature. 10-20 mL ethyl acetate was added. The organic phase was extracted with water (3×10 mL). The aqueous phases were combined and acidified with 1M aqueous HCl solution to pH 1-2. The aqueous phase was extracted with dichloromethane. The organic phase was dried on hydrophilic cotton then evaporated to dryness to give compound Ia-11 in the form of a blue powder (70 mg, 90%).

Characterization of Compound Ia-11

$^1$H NMR (CDCl$_3$ 300 MHz): 1.41 (s, 6H), 3.15 (m, 4H), 3.20 (s, 6H), 3.41 (s, 6H), 3.52 (m, 4H), 3.60 (m, 4H), 3.74 (m, 4H), 3.90 (m, 4H), 4.17 (s, 4H), 4.22 (m, 4H), 6.63 (s, 2H),

To a solution of compound Ia-8 (80 mg, 0.10 mmol) in 20 mL ethanol, 162 mg sodium hydroxide (4.05 mmol) was added. The solution was stirred overnight at room temperature. 10-20 mL ethyl acetate was added. The organic phase was extracted with water (3×10 mL). The aqueous phases were combined and acidified with 1M aqueous HCl solution to pH 1-2. The aqueous phase was extracted with dichloromethane. The organic phase was dried on hydrophilic cotton then evaporated to dryness to yield compound Ia-12 in the form of an orange powder (70 mg, 90%).

Characterization of compound Ia-12

$^1$H NMR (CDCl$_3$ 300 MHz): 1.36 (s, 3H), 1.39 (s, 3H), 2.74 (s, 3H), 3.26 (s, 6H), 3.32 (m, 4H), 3.40 (s, 3H), 3.56 (m, 6H), 3.73 (m, 2H), 3.88 (m, 2H), 4.18 (m, 6H), 6.03 (s, 1H), 6.59 (s, 1H), 7.22 (AB sys, 4H, J$_{AB}$=8.67 Hz, u$_o$δ=180.18 Hz); 7.58 (AB sys, 2H, J$_{AB}$=16.29 Hz, u$_o$δ=297.72 Hz), 7.85 (AB sys, 4H, J$_{AB}$=7.99 Hz, u$_o$δ=226.28 Hz).

$^{13}$C NMR (CDCl$_3$, 300 MHz): δ=14.86, 15.08, 16.37, 29.79, 58.91, 59.18, 59.58, 67.63, 68.41, 69.79, 70.88, 71.69, 72.05, 91.43, 128.76, 129.06, 129.69, 130.15, 130.44, 130.86, 134.10, 138.65, 140.39, 140.59, 141.25, 152.61, 155.54, 159.61, 170.40.

UV-Vis (PBS buffer) λ nm (ε, M$^{-1}$ cm$^{-1}$)=564 (70000), 338 (25000);

Preparation of Compound Ia-13

Compound Ia-13 was prepared according to the following reaction scheme:

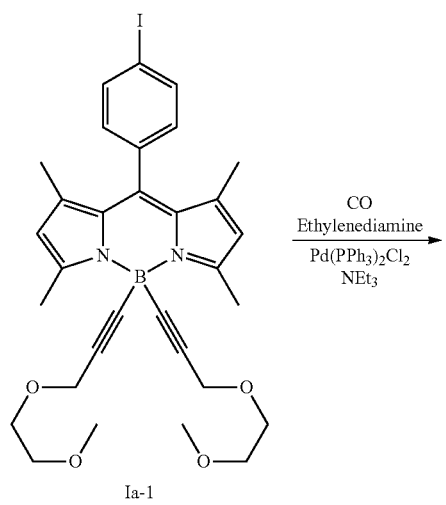

To a solution of compound Ia-13 (200 mg, 0.31 mmol) in 15 mL benzene were added 1 mL ethylenediamine (15 mmol), 66 mg bis(triphenylphosphine) palladium bis-chloride (0.09 mmol) and 1 mL de triethylamine. The solution was stirred at 70° C. overnight with carbon monoxide <<bubbling>>. The reaction mixture was extracted with dichloromethane and washed with water (3×20 mL). The organic phase was dried on hydrophilic cotton and evaporated. The residue was purified by column chromatography on silica gel (100% CH$_2$Cl$_2$ gradient with CH$_2$Cl$_2$ 75:25) to give compound Ia-13 in the form of an orange powder (160 mg, 80%).

Characterization of Compound Ia-13

$^1$H NMR (CDCl$_3$, 300 MHz): δ=1.34 (s, 6H), 2.72 (s, 6H), 3.01 (t, 2H, $^3$J=5.7 Hz), 3.36 (s, 6H), 3.55 (m, 6H), 3.64 (m, 4H), 4.20 (s, 4H), 6.01 (s, 2H), 6.98 (t, 1H, $^3$J=5.5 Hz), 7.69 (AB sys, 4H, J$_{AB}$=8.3 Hz, v$_o$δ=162.7 Hz);

$^{13}$C {$^1$H} NMR (CDCl$_3$, 75.4 MHz): δ=15.0, 16.2, 41.3, 42.2, 59.1, 59.8, 68.7, 71.9, 90.6, 121.9, 127.9, 128.8, 129.4, 134.9, 139.1, 140.4, 141.0, 155.7, 167.0;

$^{11}$B NMR (CDCl$_3$, 128.4 MHz): δ=−10.3 (s);

UV-Vis (CH$_2$Cl$_2$) λ nm (ε, M$^{-1}$ cm$^{-1}$)=500 (64500), 371 (5600)

FAB$^+$ m/z: 599.2 ([M+H]$^+$, 100);

Elementary analysis calculated for C$_{34}$H$_{43}$BN$_4$O$_5$: C, 68.23; H, 7.24; N, 9.36. Found: C, 67.84; H, 7.07; N, 9.22.

Preparation of Compound Ia-14

Compound Ia-14 was prepared according to the following reaction scheme:

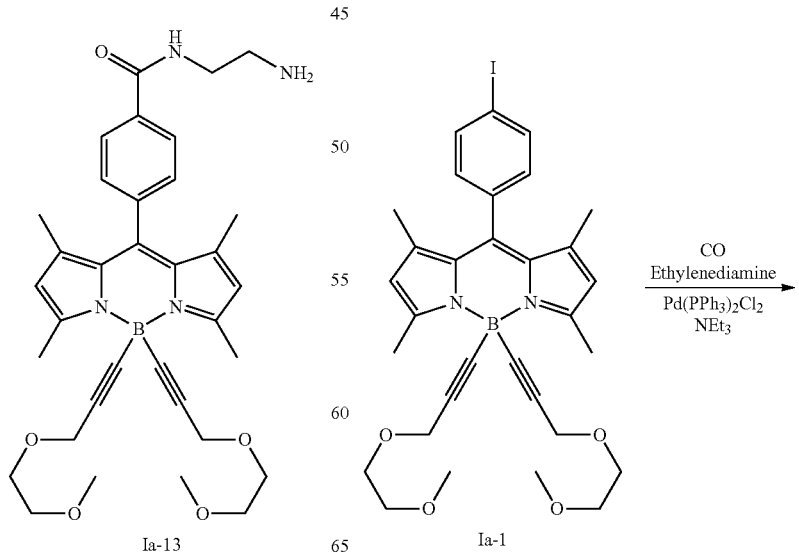

Preparation of Compound Ia-15

Compound Ia-15 was prepared according to the following reaction scheme:

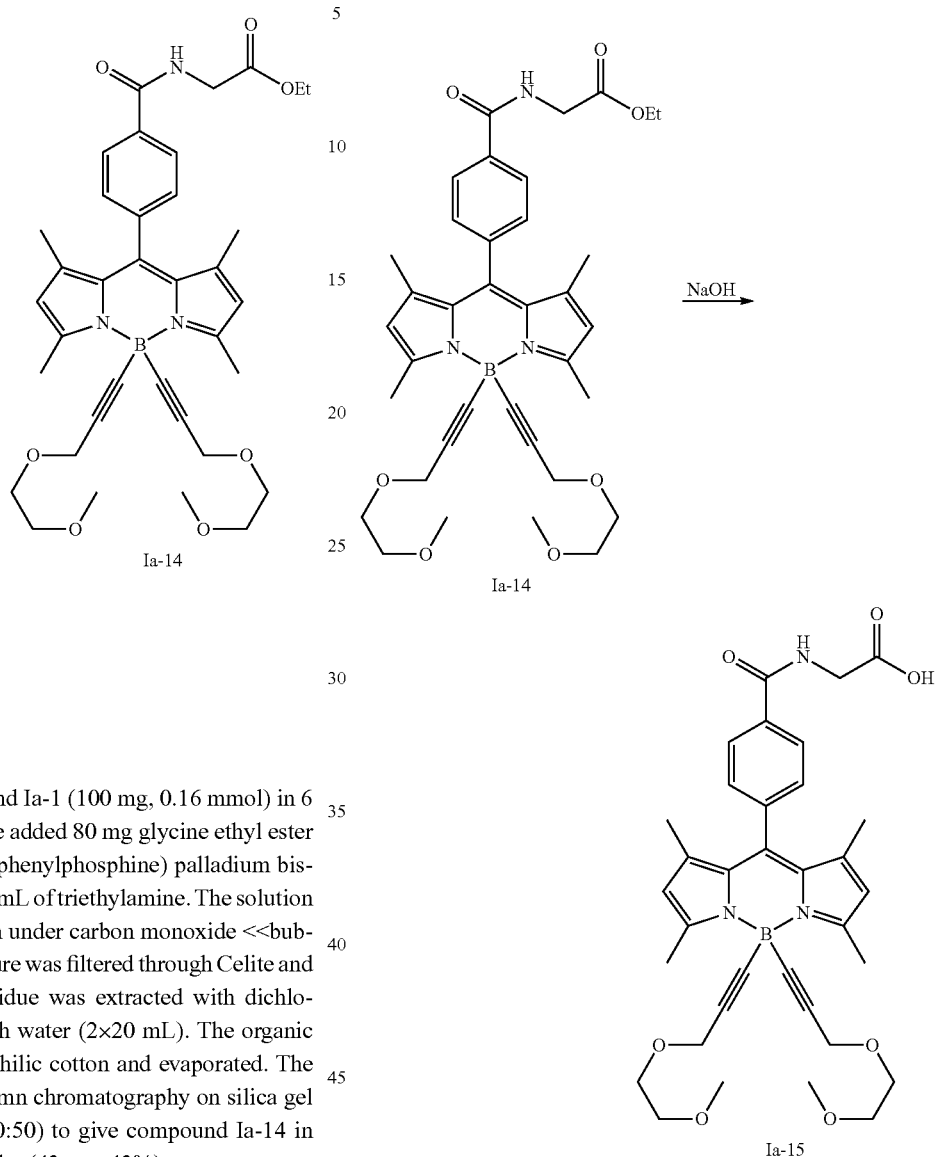

To a solution of compound Ia-1 (100 mg, 0.16 mmol) in 6 mL anhydrous toluene were added 80 mg glycine ethyl ester (0.47 mmol), 22 mg bis(triphenylphosphine) palladium bischloride (0.03 mmol) and 2 mL of triethylamine. The solution was stirred at 80° C. for 6 h under carbon monoxide <<bubbling>>. The reaction mixture was filtered through Celite and partly evaporated. The residue was extracted with dichloromethane and washed with water (2×20 mL). The organic phase was dried on hydrophilic cotton and evaporated. The reside was purified by column chromatography on silica gel (AcOEt/Petroleum ether 50:50) to give compound Ia-14 in the form of an orange powder (43 mg, 43%).

Characterization of Compound Ia-14

$^1$H NMR (CDCl$_3$, 300 MHz): δ=1.33 (t, 3H, $^3$J=7.2 Hz), 1.34 (s, 6H), 2.72 (s, 6H), 3.36 (s, 6H), 3.55 (m, 4H), 3.66 (m, 4H), 4.20 (s, 4H), 4.27 (d, 2H, $^3$J=4.5 Hz), 4.29 (q, 2H, $^3$J=7.1 Hz), 6.01 (s, 2H), 6.77 (t, 1H, $^3$J=4.9 Hz), 7.69 (AB sys, 4H, J$_{AB}$=8.3 Hz, v$_o$δ=156.4 Hz);

$^{13}$C {$^1$H} NMR (CDCl$_3$, 75.4 MHz): δ=14.3, 14.9, 16.2, 42.1, 59.1, 59.8, 61.9, 68.7, 71.9, 91.0, 121.9, 127.9, 129.0, 129.3, 134.2, 139.5, 140.2, 141.0, 155.8, 166.7, 170.2;

$^{11}$B NMR (CDCl$_3$, 128.4 MHz): δ=−10.3 (s);

UV-Vis (CH$_2$Cl$_2$) λ nm (ϵ, M$^{-1}$ cm$^{-1}$)=501 (84200), 366 (4200), 309 (6500);

To a solution of compound Ia-14 (40 mg, 0.06 mmol) in ethanol (10 mL) an aqueous sodium hydroxide solution (60 mg, 1.2 mmol) was added. The solution was stirred for 2 h at room temperature. 10-20 mL ethyl acetate was added. The organic phase was extracted with water (2×20 mL). The aqueous phases were combined and acidified with 1M aqueous HCl solution to pH 1-2. The product was extracted with dichloromethane. The organic phase was dried over Na$_2$SO$_4$ then evaporated to dryness to give compound Ia-15 in the form of an orange powder (35 mg, 90%).

Characterization of Compound Ia-15

$^1$H NMR (CDCl$_3$, 400 MHz): δ=1.32 (s, 6H), 2.72 (s, 6H), 3.36 (s, 6H), 3.55 (m, 4H), 3.66 (m, 4H), 4.19 (s, 4H), 4.27 (d, 2H, $^3$J=3.4 Hz), 4.87 (b, 1H), 6.01 (s, 2H), 7.04 (t, 1H, $^3$J=3.8 Hz), 7.69 (AB sys, 4H, J$_{AB}$=6.0 Hz, v$_o$δ=160.2 Hz);

$^{13}$C {$^1$H} NMR (CDCl$_3$, 100 MHz): δ=14.9, 16.2, 42.0, 59.0, 59.7, 68.6, 71.8, 90.9, 121.9, 128.0, 129.0, 129.3, 133.8, 139.6, 140.2, 140.9, 155.8, 167.3, 172.3;

$^{11}$B NMR (CDCl$_3$, 128.4 MHz): δ=−10.2 (s);

UV-Vis (CH$_2$Cl$_2$) λ nm (ε, M$^{-1}$ cm$^{-1}$)=501 (65000), 366 (3800), 309 (5900);

UV-Vis (PBS buffer) λ nm (ε, M$^{-1}$ cm$^{-1}$)=496 (59600), 367 (4100), 308 (6100);

Preparation of Compound Ia-16

Compound Ia-16 was prepared according to the following reaction scheme:

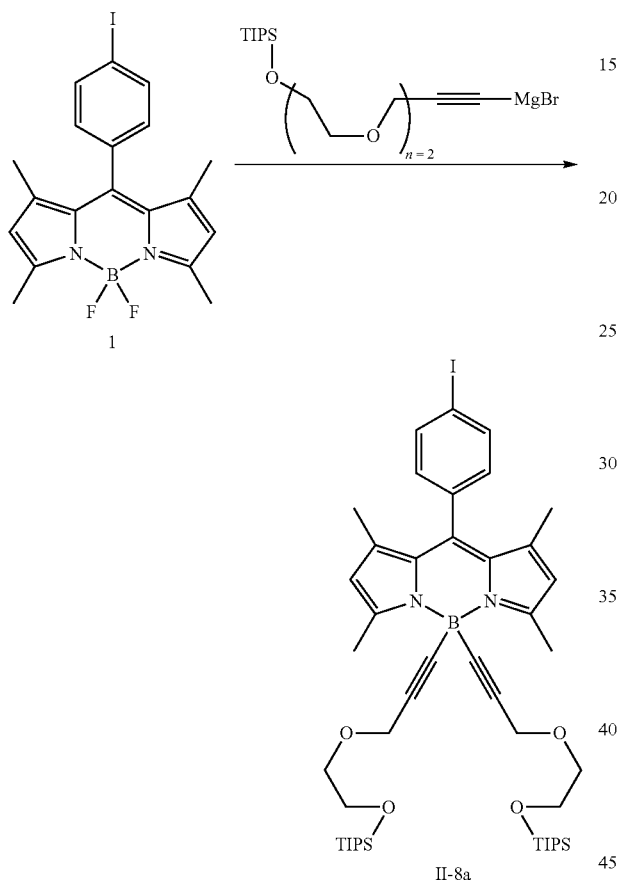

To a solution of 2-triisopropyloxysilanoxy-5-oxaoct-7-yne (2.20 mmol, 661 mg) in anhydrous THF at room temperature, ethylmagnesium bromide (1.0 M in THF, 2 ml) was added under argon. The mixture was stirred for 2 h at 60° C. then left to cool at room temperature. The solution obtained was transferred via cannula to a solution of difluoroboradipyrromethene 1 (330 mg, 0.733 mmol) in anhydrous THF. The solution was stirred overnight at 60° C., after which water was added. This solution was extracted with dichloromethane. The organic phase was next washed with water (3×20 ml) then with NaCl-saturated solution (1×20 ml). After evaporation, the organic residue was purified by column chromatography on silica gel (Ethyl acetate/Petroleum ether 10:90; 20:80; 30:70), and compound Ia-16 was obtained in the form of an orange powder (620 mg, 87%).

Characterization of Compound Ia-16

$^1$H NMR (CDCl$_3$ 300 MHz): 1.05 (m, 42H), 1.40 (s, 6H), 2.71 (s, 6H), 3.56 (t, 4H, $^3$J=5.70 Hz), 3.65 (s, 8H), 3.82 (t, 4H, $^3$J=5.70 Hz), 4.18 (s, 4H), 6.00 (S, 2H), 7.45 (AB sys, 4H, J$_{AB}$=8.28 Hz, u$_o$δ=227.51 Hz);

$^{13}$C NMR (CDCl$_3$, 300 MHz): δ=12.13, 14.97, 16.21, 18.11, 59.77, 63.07, 68.99, 70.80, 72.86, 77.36, 94.60, 121.84, 129.45, 130.39, 135.30, 138.34, 140.11, 140.92, 155.67.

Preparation of Compound Ia-17

Compound Ia-17 was prepared according to the following reaction scheme:

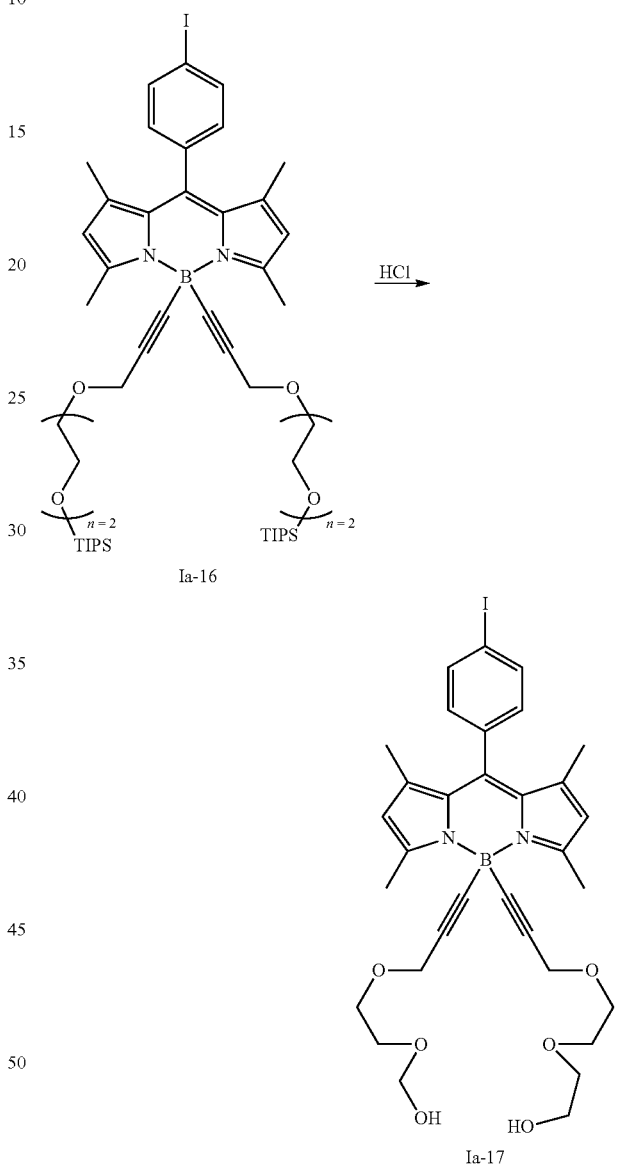

To a solution of compound Ia-16 (300 mg, 2.96 mmol) in ethanol (15 mL) an aqueous 1M solution of hydrochloric acid was added (10 ml). The solution was stirred overnight at room temperature. The organic phase was then neutralized with NaHCO$_3$ solution to pH 7. The reaction medium was then evaporated in a rotary evaporator, dissolved in CH$_2$Cl$_2$ then washed with saturated NaCl solution (2×15 ml). The organic phase was dried over Na$_2$SO$_4$ then evaporated to dryness. The reaction product was purified by column chromatography on silica gel (Ethyl acetate/Methanol, 95:5%) and an orange powder was obtained (200 mg, 81%)

Characterization of Compound Ia-17

$^1$H NMR (CDCl$_3$ 200 MHz): 1.39 (s, 6H), 2.72 (s, 6H), 3.67 (m, 16H), 4.18 (s, 4H), 6.02 (s, 2H), 7.44 (AB sys, 4H, J$_{AB}$=8.15 Hz, u$_o$δ=152.97 Hz)

$^{13}$C NMR (CDCl$_3$, 200 MHz): δ=14.99, 16.22, 59.76, 61.89, 68.92, 70.44, 72.59, 77.35, 94.67, 121.87, 123.37, 129.40, 130.30, 135.13, 138.36, 140.21, 141.09, 155.63, 197.65.

Preparation of Compound Ia-18

Compound Ia-18 was prepared according to the following reaction scheme:

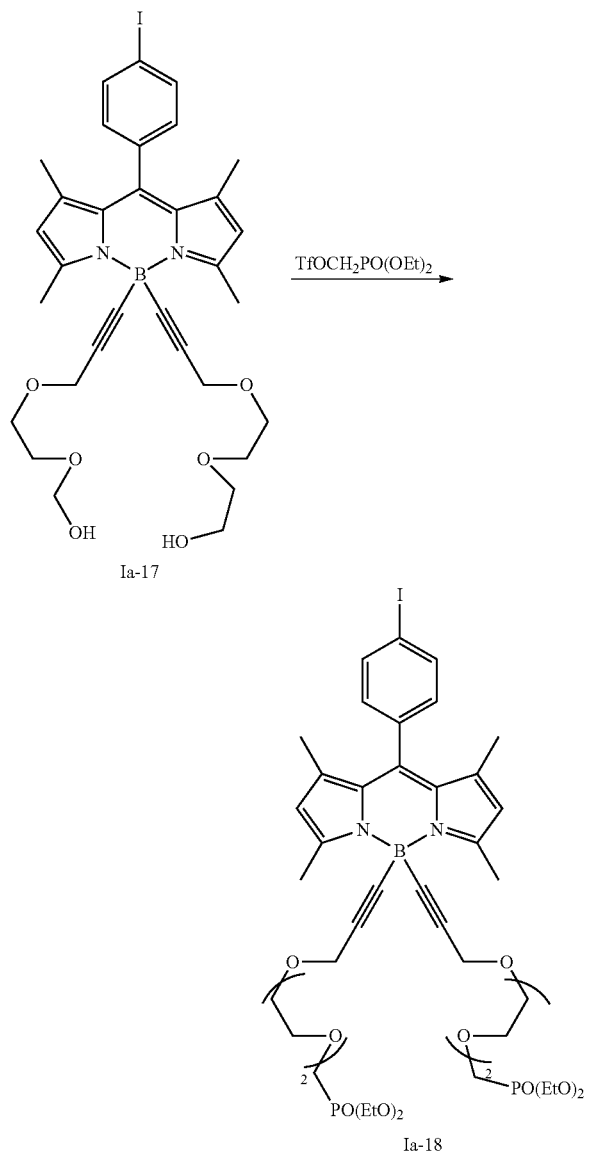

To a solution of compound Ia-17 (200 mg, 0.241 mmol) in anhydrous THF (20 ml), a THF solution (10 ml) with tBuOK in suspension (54 mg, 0.241 mmol) was added by cannula. Immediately afterwards 5 ml (155 mg, 0.29 mmol) of phosphonate solution in THF was added. The mixture was stirred at room temperature for 30 min after which the same quantities of reagents were added to obtain a total of 3 equivalents in excess.

The reaction medium was then neutralized with 30 ml 1M aqueous HCl solution and extracted with 2×30 ml dichloromethane. The organic phase was then washed with 2×10 ml water and 1×10 ml saturated NaCl solution. The organic phases were combined then dried on hydrophilic cotton and evaporated to dryness. The reaction product was purified by column chromatography on silica gel (Ethyl Acetate/Methanol, 100%; 99:1; 98:2; 97:3; 94:6) to give compound Ia-18 in the form of an orange oil (135 mg, 50%)

Characterization of Compound Ia-18

$^1$H NMR (CDCl$_3$ 200 MHz): 1.33 (t, 12H, $^3$J=7.25 Hz), 1.40 (s, 6H), 2.70 (s, 6H), 3.75 (m, 16H), 3.83 (d, 4H $^2$J=8 Hz), 4.15 (m, 12H), 6.01 (s, 2H), 7.45 (AB sys, 4H, J$_{AB}$=7.93 Hz, u$_o$δ=152.88 Hz);

Preparation of Compound Ic-0

Compound Ic-0 was prepared according to the following reaction scheme:

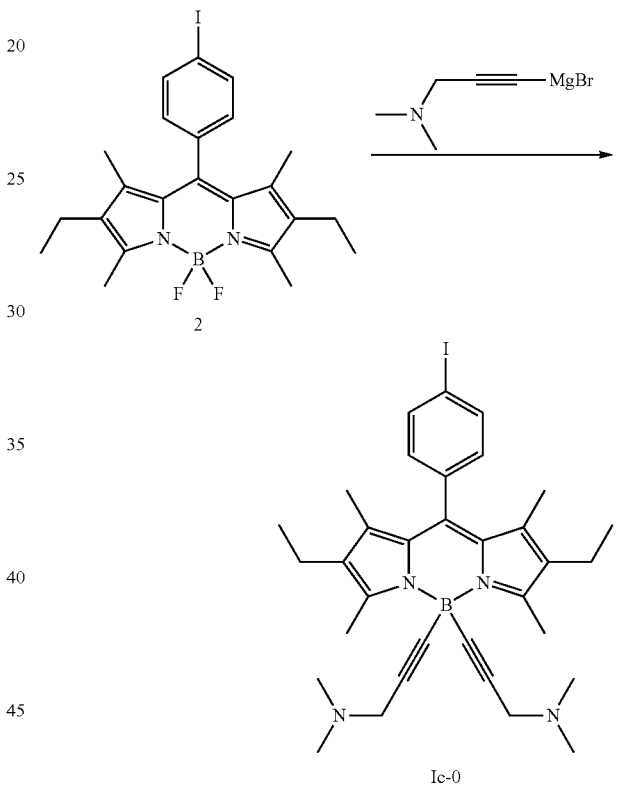

To a solution of 1-dimethylamino-2-propyn (0.136 g, 1.976 mmol) in anhydrous THF (5 ml), EtMgBr in THF (1.738 ml, 1.0 M) was added under argon at 60° C. for 2 hours. This mixture was then transferred by cannula to a solution of 2,6-diethyl-4,4-difluoro-1,3,5,7-tetramethyl-8-(4'-iodo-phenyl)-4-bora-3a,4a-diaza-s-indacene 2 (0.400 g, 0.79 mmol) in anhydrous THF (3 ml). The mixture was stirred at 60° C. for 30 minutes after which water H$_2$O (3 ml) was added and the mixture extracted with CH$_2$Cl$_2$. After evaporation, column chromatography on silica gel (CH$_2$Cl$_2$/AcOEt, 50:50 then MeOH/AcOEt, 1:9) allowed pure Ic-0 to be obtained (0.313 g, 63%).

Characterization of Compound Ic-0

$^1$H NMR (CDCl$_3$ 300 MHz): 0.97 (t, 6H, $^3$J=7.53 Hz), 1.30 (s, 6H), 2.32 (q, 4H, $^3$J=7.14 Hz), 2.38 (s, 12H), 2.72 (s, 6H), 3.30 (s, 4H), 7.06 (AB sys, 2H, J$_{AB}$=8.31 Hz), 7.81 (AB sys, 2H, J$_{AB}$=8.31 Hz);

$^{13}$C NMR (CDCl$_3$, 75 MHz): δ=12.11, 14.12, 14.69, 17.32, 29.36, 43.73, 48.78, 94.29, 128.69, 130.50, 133.03, 135.87, 136.07, 138.10, 138.52, 153.63.

MS (FAB', m-NBA): m/z (%)=633.1 [M+H]$^+$ (100).

Analysis calculated for C$_{33}$H$_{42}$BIN$_4$: C, 62.67; H, 6.69; N, 8.86. Found: C, 62.52; H, 6.5; N, 8.53.

Optical Properties:

ζ(CH$_2$Cl$_2$)=6.6 ns.

UV-vis (CH$_2$Cl$_2$): λ$_{ab}$ (ε)=521 (57000), 378 (4500).

Fluorescence (CH$_2$Cl$_2$): 6.1×10$^{-7}$ M. λ$_{em}$=533 nm, φ=48%.

Preparation of Compound Ic-1

Compound Ic-1 was prepared according to the following reaction scheme:

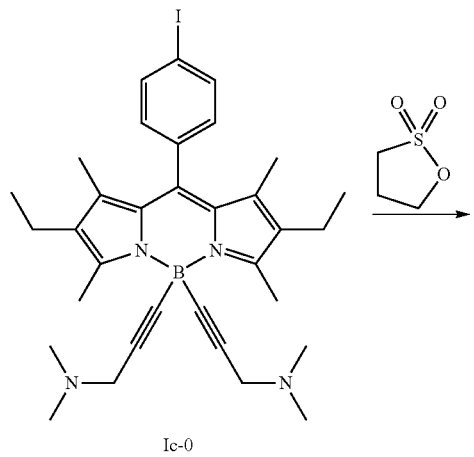

To a solution of Ic-0 (0.050 g, 0.079 mmol) in anhydrous toluene (3 ml), 1,3-propane Sultone (0.024 g, 0.20 mmol) was added under argon and the mixture was left under stirring at 60° C. overnight until complete disappearance of the starting material (controlled by TLC). The suspension was centrifuged and then washed with toluene (5 ml) and pentane (5 ml). After drying the powder in vacuo, the pure compound Ic-1 was obtained (0.086 g, 62%).

Characterization of Compound Ic-1

$^1$H NMR (CD$_3$OD 300 MHz): 0.99 (t, 6H, $^3$J=7.53 Hz), 1.37 (s, 6H), 2.20 (m, 4H), 2.39 (q, 4H, $^3$J=7.53 Hz), 2.72 (s, 6H), 2.82 (t, 4H, $^3$J=6.99 Hz), 3.56 (m, 4H), 4.30 (s, 4H), 7.13 (AB sys, 2H, J$_{AB}$=8.28 Hz), 7.93 (AB sys, 2H, J$_{AB}$=8.28 Hz);

$^{13}$C NMR (CD$_3$OD, 75 MHz): δ=10.93, 13.45, 13.59, 16.59, 18.72, 29.27, 49.71, 55.16, 62.68, 94.12, 116.51, 128.66, 130.33, 133.64, 135.09, 137.26, 138.37, 139.59, 153.55.

MS (FAB', m-NBA): m/z (%)=876.1 [M+H]$^+$ (100).

Analysis calculated for pour Ic-1 +H$_2$O, C$_{39}$H$_{58}$BIN$_4$O$_8$S$_2$. C, 51.32; H, 6.40; N, 6.14;

Found: C, 51.27; H, 6.28; N, 5.82.

Optical Properties:

ζ(H$_2$O)=7.0 ns.

UV-vis (PBS buffer): λ$_{ab}$ (ε)=519 (28700), 564 (15000).

Fluorescence (PBS buffer): 4.6×10$^{-7}$ M. λ$_{em}$=530 nm, φ=61%.

UV-vis (EtOH): λ$_{ab}$ (ε)=521 (81200), 240 (34400).

Fluorescence (EtOH): 3.99×10$^{-7}$ M. λ$_{em}$=532 nm, φ=71%.

Preparation of Compound Ic-2

Compound Ic-2 was prepared according to the following reaction scheme:

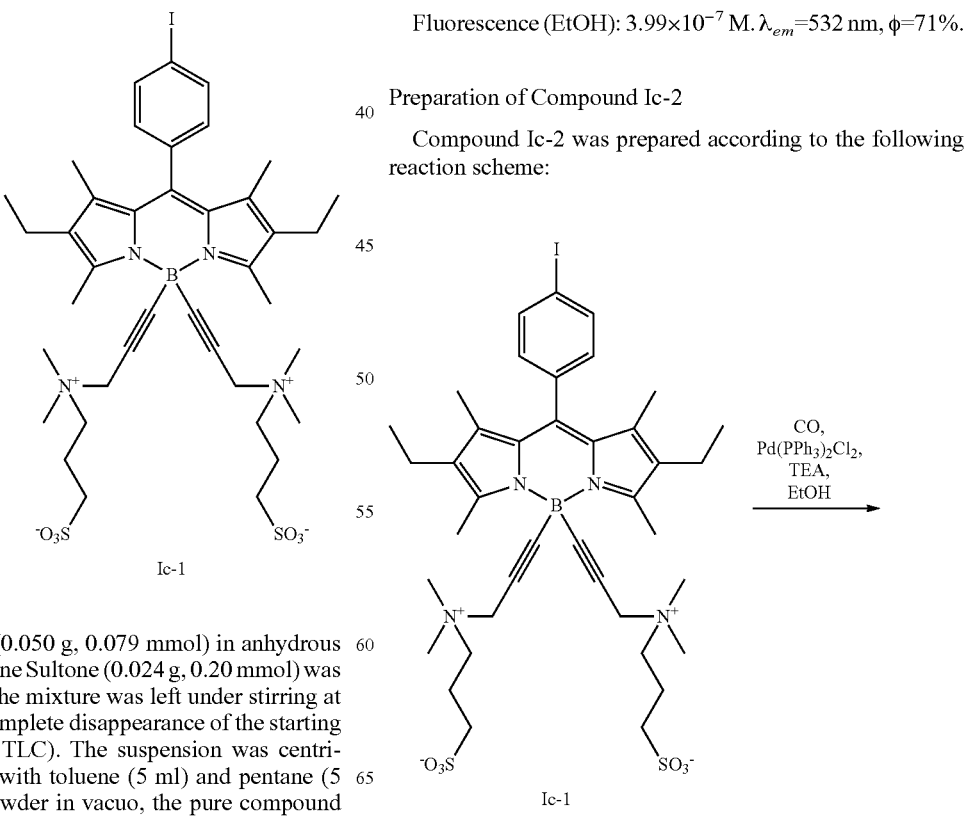

Preparation of Compound Ic-3

Compound Ic-3 was prepared according to the following reaction scheme:

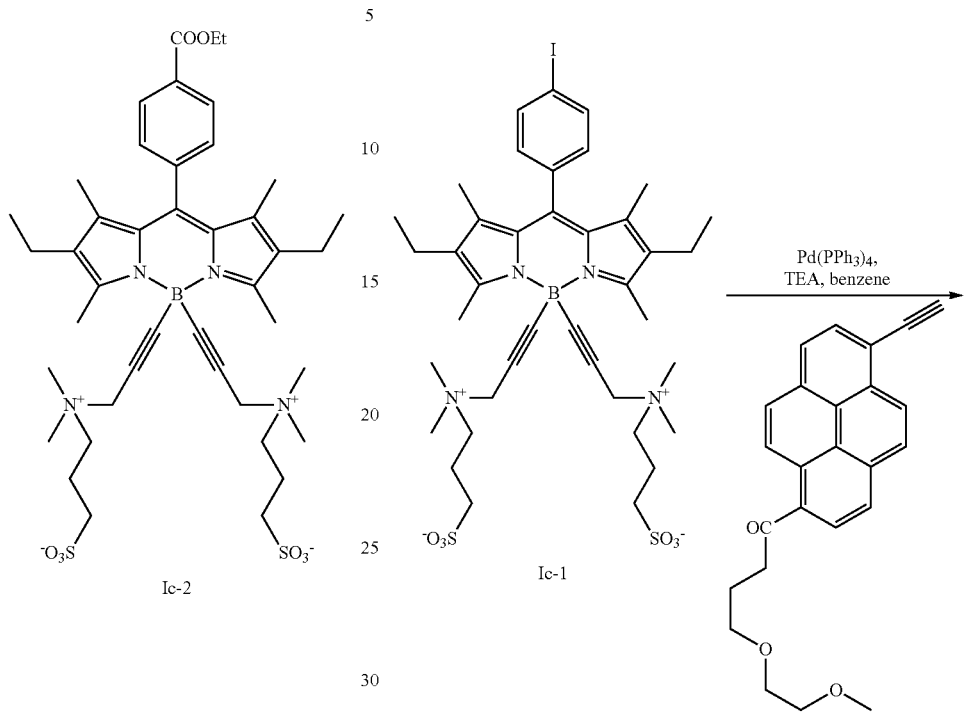

To a solution of Ic-1 (0.040 g, 0.457 mmol) with absolute ethanol (4 ml), triethylamine (3 ml) and Pd(PPh$_3$)$_2$Cl$_2$ (4 mg, 0.046 mmol) were injected at 70° C. under CO bubbling for 4 hours. After evaporation of the solvent, chromatography on silica (H$_2$O/EtOH, 20:80) followed by re-crystallisation in a methanol-Et$_2$O mixture allowed product Ic-2 to be obtained (20 mg, 54%).

Characterization of Compound Ic-2

$^1$H NMR (CD$_3$OD 300 MHz): 1.01 (t, 6H, $^3$J=7.53 Hz), 1.33 (s, 6H), 1.43 (t, 3H, $^3$H=7.17 Hz), 2.24 (m, 4H), 2.40 (q, 4H, $^3$J=7.53 Hz), 2.75 (s, 6H), 2.85 (m, 4H), 3.18 (s, 12H), 3.61 (m, 4H), 4.32 (s, 4H), 4.43 (q, 2H, $^3$J=7.17 Hz), 7.50 (AB sys, 2H, J$_{AB}$=8.28 Hz), 8.21 (AB sys, 2H, J$_{AB}$=8.49 Hz);

$^{13}$C NMR (CD$_3$OD, 75 MHz): δ=6.22, 10.84, 13.19, 13.47, 13.57, 16.57, 18.71, 21.68, 22.63, 30.67, 31.64, 37.27, 49.71, 52.55, 53.39, 55.19, 61.10, 62.71, 128.15, 128.45, 128.79, 130.04, 133.70, 137.22, 153.69, 179.87.

UV-vis (EtOH): λ$_{ab}$ (ε)=521 (15339), 240 (2740).

Fluorescence (EtOH): 4.56×10$^{-7}$ M. λ$_{em}$=533 nm, φ=45%.

A solution of Ic-1 (0.060 g, 0.068 mmol) in DMF (5 ml) and NEt₃ (4 ml) was degassed with argon for 20 min, followed by the addition of [Pd (PPh₃)₄] (0.008 g, 0.0070 mmol) and 1-ethynyl-6-methoxydiethyleneglycol carboxylatepyrene (0.31 g, 0.082 mmol). The mixture was stirred at 80° C. for 36 hours until full consumption of the starting material as observed by TLC (H₂O/EtOH, 20:80). The mixture was then evaporated to dryness and the residue dissolved in 3 ml of $CH_2Cl_2$ then precipitated with $Et_2O$. Re-crystallisation in $CH_3OH-Et_2O$ allowed the pure product to be obtained (40 mg, 50%).

Characterization of Compound Ic-3

$^1$H NMR (CD₃OD 300 MHz): 1.03 (t, 6H, $^3J$=7.53 Hz), 1.47 (s, 6H), 2.25 (m, 4H), 2.40 (q, 4H, $^3J$=7.53 Hz), 2.77 (s, 6H), 2.86 (t, 4H, $^3J$=6.78 Hz), 3.17 (s, 12H), 3.39 (s, 3H), 3.62 (m, 6H), 3.78 (m, 2H), 3.98 (m, 2H), 4.34 (s, 4H), 4.47 (m, 2H), 7.47 (AB sys, 2H, $J_{AB}$=8.10 Hz), 7.94 (AB sys, 2H, $J_{AB}$=8.28 Hz), 8.27 (m, 5H), 8.65 (d, 1H, $^3J$=9.42 Hz), 8.75 (d, 1H, $^3J$=9.21 Hz), 9.20 (d, 1H, $^3J$=9.39 Hz).

Optical Properties:

UV-vis (EtOH): $\lambda_{ab}$ ($\epsilon$)=521 (60936), 402 (35224), 380 (37255), 291(25567).

Fluorescence (EtOH): 3.79×10⁻⁷ M. $\lambda_{em}$=533 nm, φ=39%.

Preparation of Compound IV-5c

Compound IV-5c was prepared according to the following reaction scheme:

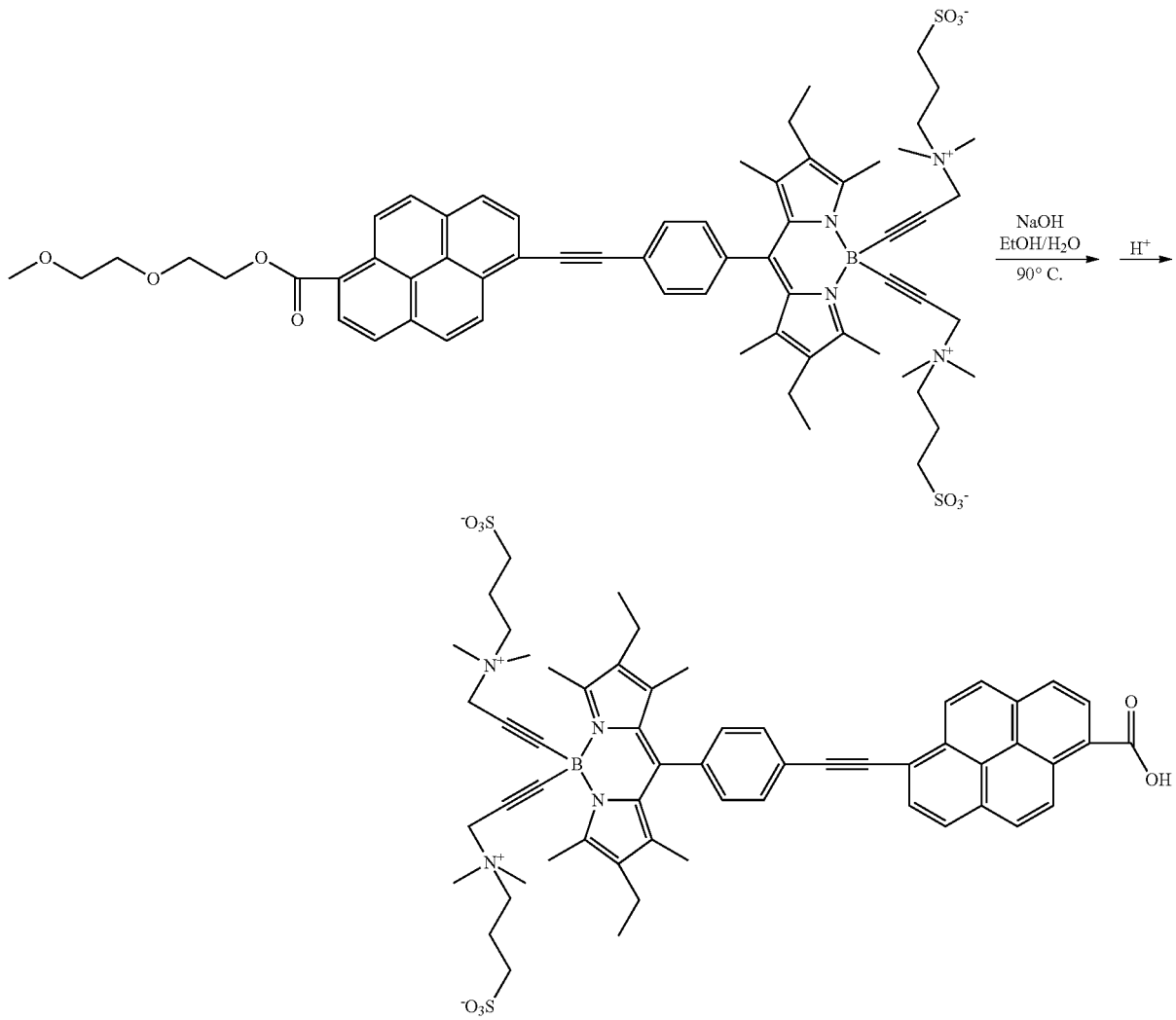

To a solution of compound IV-5b (0.030 g, 0.026 mmol) in ethanol (2 ml) and water (1 ml), NaOH (0.020 g, 0.05 mmol) was added. The mixture was heated to 80° C. for 40 minutes. The solution was then neutralized to pH 4 with an aqueous HCl solution (10%). After evaporation, column chromatography (silica, H₂O/EtOH, 10:90) allowed compound IV-6b to be obtained in powder form (20 mg, 75%).

Characterization of Compound IV-6b $^1$H NMR (CD₃OD 200 MHz): 1.01 (t, 6H, $^3J$=7.30 Hz), 1.45 (s, 6H), 2.04-2.22 (m, 8H), 2.74-2.86 (m, 9H), 3.14 (s, 12H), 3.59 (m, 5H), 4.30 (s, 4H), 7.43 (AB sys, 2H, $J_{AB}$=8.40 Hz), 7.90 (AB sys, 2H, $J_{AB}$=8.40 Hz), 8.10-8.27 (m, 6H), 8.66 (d, 1H, $^3J$=9.14 Hz), 8.84 (d, 1H, $^3J$=9.12 Hz).

MS (FAB', m-NBA): m/z (%)=1041.46 [M+Na]⁺ (100)

All the synthesized compounds in the above examples are fluorescent and hydrophilic. The compounds with an asterisk * are water-soluble and have a solubility of more than 10 mg/L, even more than 50 mg/L for Ia-9, Ia-10, Ic-1. The values of the fluorescence properties of some of the exemplified compounds are given in Table 1 below:

TABLE 1

| N° | $\lambda_{abs}$ (nm) | $\lambda_{em}$ (nm) | $\epsilon(M^{-1}cm^{-1})$ | $\Phi(\%)$ |
|---|---|---|---|---|
| Ia-1 | 500 | 511 | 90000 | 65 |
| Ia-2 | 522 | 488 | 82000 | 80 |
| Ia-3 | 646 | 371 | 126600 | 75 |
| Ia-4 | 572 | 533 | 93500 | 80 |
| Ia-5 | 500 | 512 | 91000 | 63 |
| Ia-6 | 522 | 488 | 80000 | 85 |
| Ia-9 | 501 | 513 | 78500 | 50 |
|  | 494* | 506* | 74000* | 60* |
| Ia-10 | 517* | 530* | 65000* | 70* |
| Ia-11 | 647 | 662 | 118000 | 74 |
| Ia-12 | 564* | 578* | 70000* | 70* |
| Ia-13 | 500 | 513 | 65000 | 30 |
| Ia-14 | 501 | 511 | 84000 | 80 |
| Ia-15 | 501 | 511 | 67000 | 60 |
|  | 495* | 507* | 62000* | 50* |
| Ic-1* | 519* | 530* | 72000* | 61* |

Values obtained in dichloromethane except for those with an asterisk*, measured in water and PBS buffer.

The invention claimed is:

1. A compound of formula (I):

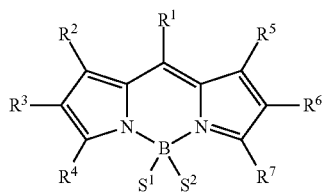

(I)

wherein:

$S^1$ is a group of formula —C≡C-L'-A in which:

L' is a linkage group which is
a single bond, or
a divalent hydrocarbon group chosen from the group consisting of straight or branched alkylenes optionally comprising one or more oxygen, nitrogen or sulphur atoms in their chain; straight or branched alkenylenes; straight or branched alkynylenes, and arylenes; or a divalent hydrocarbon chain composed of a chain of at least two divalent hydrocarbon groups of the aforementioned type;

A is a polar functional group chosen from among sulphonate, sulphate, phosphate, ammonium, carboxylate, phosphonate, alkylammonium sulphate and polyoxyethylene groups;

$S^2$ is:
a —C≡C-L'-A group identical to or different from $S^1$, in which L' and A have the aforementioned meanings;
—F;
—H; or
a hydrocarbon chain, straight or branched, saturated or unsaturated, optionally interrupted by one or more oxygen, nitrogen or sulphur atoms, optionally cyclized in whole or in part, optionally aromatic and optionally functionalized, and each of groups $R^1$, $R^2$, $R^3$, $R^4$, $R^5$, $R^6$ or $R^7$ each independently designates a —H group or a hydrocarbon chain, wherein the hydrocarbon chain is straight or branched, saturated or unsaturated, optionally interrupted by one or more oxygen atoms, optionally cyclized in whole or in part, optionally aromatic and/or optionally functionalized, provided that all or part of $R^1$, $R^2$, $R^3$, $R^4$, $R^5$, $R^6$ or $R^7$ can be linked together to form a bridged form.

2. The compound according to claim 1, wherein the functional A group present as $S^1$ group on the —C≡C-L'-A group, is selected from the group consisting of polyoxyethylene, phosphate, sulphate and alkylammonium sulphate groups.

3. The compound according to claim 1, wherein $S^1$ and $S^2$ are the same.

4. The compounds according to claim 1, of following formula (II):

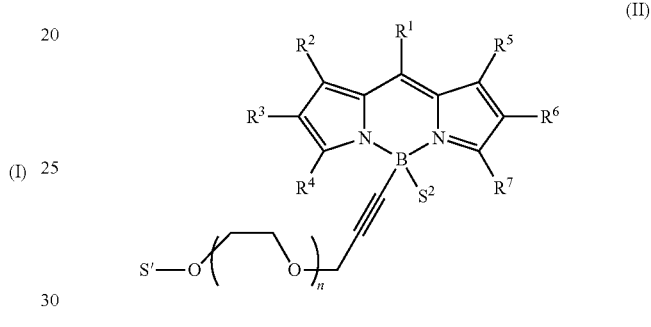

(II)

wherein:

$S^2$ is:
a —C≡C-L'-A group identical to or different from $S^1$, in which L' and A have the aforementioned meanings;
—F;
—H; or
a hydrocarbon chain, straight or branched, saturated or unsaturated, optionally interrupted by one or more oxygen, nitrogen or sulphur atoms, optionally cyclized in whole or in part, optionally aromatic and optionally functionalized, and each of groups $R^1$, $R^2$, $R^3$, $R^4$, $R^5$, $R^6$ or $R^7$ each independently designates a —H group or a hydrocarbon chain, straight or branched, saturated or unsaturated, optionally interrupted by one or more oxygen atoms, optionally cyclized in whole or in part, optionally aromatic and optionally functionalized, provided that all or part of $R^1$, $R^2$, $R^3$, $R^4$, $R^5$, $R^6$ or $R^7$ can be linked together to form a bridged form, n is 1, 2, 3 or 4, $S^1$ is —H, -Me—$(CH_2)_{n'}$—$SO_3^-(X^{m+})_{1/m}$ or —$(CH_2)_{n'}$—$PO_3^{2-}(X^{m+})_{2/m}$ in which:

$X^{m+}$ is a cation (mono- or polyatomic cation) of valence m, n' is an integer of 1, 2, 3 or 4.

5. The compounds according to claim 1, of following formula (III):

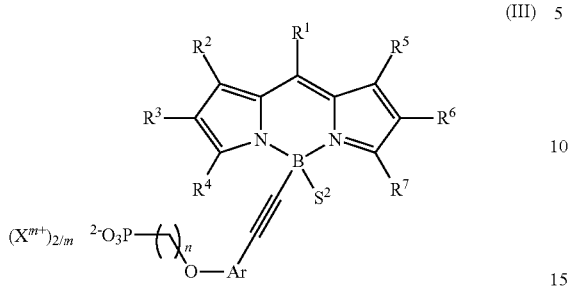

wherein:
S² is:
- a —C≡C-L'-A group identical to or different from S¹, in which L' and A have the aforementioned meanings;
- —F;
- —H; or
- a hydrocarbon chain, straight or branched, saturated or unsaturated, optionally interrupted by one or more oxygen, nitrogen or sulphur atoms, optionally cyclized in whole or in part, optionally aromatic and optionally functionalized, and each of groups $R^1$, $R^2$, $R^3$, $R^4$, $R^5$, $R^6$ or $R^7$ each independently designates a —H group or a hydrocarbon chain, straight or branched, saturated or unsaturated, optionally interrupted by one or more oxygen atoms, optionally cyclized in whole or in part, optionally aromatic and optionally functionalized, provided that all or part of $R^1$, $R^2$, $R^3$, $R^4$, $R^5$, $R^6$ or $R^7$ can be linked together to form a bridged form, Ar is an arylene,
$X^{m+}$ is a cation (mono- or polyatomic) of valence m,
n' is an integer of 1, 2, 3 or 4.

6. The compounds according to claim 1, of following formula (IV):

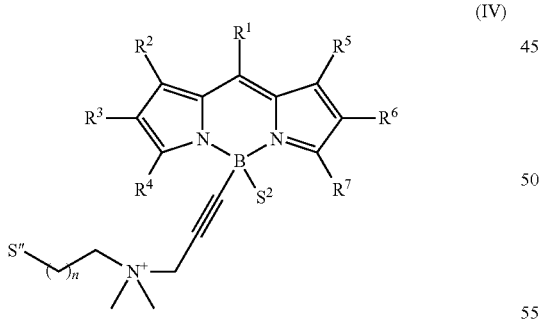

wherein:
S² is:
- a —C≡C-L'-A group identical to or different from S¹, in which L' and A have the aforementioned meanings;
- —F;
- —H; or
- a hydrocarbon chain, straight or branched, saturated or unsaturated, optionally interrupted by one or more oxygen, nitrogen or sulphur atoms, optionally cyclized in whole or in part, optionally aromatic and optionally functionalized, and each of groups $R^1$, $R^2$, $R^3$, $R^4$, $R^5$, $R^6$ or $R^7$ each independently designates a —H group or a hydrocarbon chain, straight or branched, saturated or unsaturated, optionally interrupted by one or more oxygen atoms, optionally cyclized in whole or in part, optionally aromatic and optionally functionalized, provided that all or part of $R^1$, $R^2$, $R^3$, $R^4$, $R^5$, $R^6$ or $R^7$ can be linked together to form a bridged form, n is 0, 1, 2, 3, 4 or 5,
S" is —SO₃⁻ or —PO₃²⁻$(X^{m+})_{1/m}$
where $X^{m+}$ is a cation (mono- or polyatomic) of valence m.

7. The compounds according to claim 1 wherein at least one of the groups $R^1$, $R^2$, $R^3$, $R^4$, $R^5$, $R^6$ or $R^7$ is a group carrying a polar functional group selected from the group consisting of carboxylate, suphonate, sulphate, phosphate, ammonium, hydroxyl, phosphonate and polyoxyethylene groups.

8. The compound according to claim 1, wherein $R^1$ is an —Ar-L-Y group where:
Ar is an arylene,
L is a single bond, a straight or branched alkylene or a substituted straight or branched alkynylene,
Y is —Cl, —Br, —I, —COOH, —COOMe, —COOEt, —CONH—CH₂—CH₂—NH₂, —CONH—CH₂—COOEt, —CONH—CH₂—COOH, —CONH—(CH₂)$_q$—NCS or else a group meeting one of the following formulas:

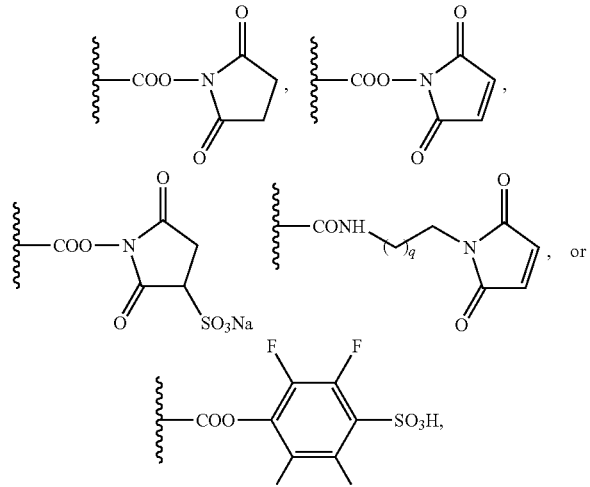

where q is 1, 2, 3, 4 or 5.

9. The compound according to claim 1, wherein:
the groups $R^2$ and $R^5$ are each independently —H or -Me groups, and
the groups $R^3$, $R^4$, $R^6$ and $R^7$ are each independently selected from the group consisting of —H, -Me, —C≡C—CH₂—N⁺(Me)₂-(CH₂)$_n$—SO₃⁻, —C≡C—Ar—R' and a group of formula

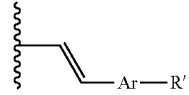

where:
   Ar is an arylene,
   R' is —OMe, —CH$_2$—PO$_3{}^{2-}$(X$^{m+}$)$_{2/m}$ or —C≡C—CH$_2$—R", in which R" is —O—(CH$_2$—CH$_2$—O)$_n$—CH$_3$,   —O—(CH$_2$—CH$_2$—O)$_n$—CH$_2$—PO$_3{}^{2-}$(X$^{m+}$)$_{2/m}$,   —O—(CH$_2$—CH$_2$—O)$_n$—CH$_2$—SO$_3{}^-$(X$^{m+}$)$_{1/m}$,   —N$^+$(Me)$_2$-CH$_2$—(CH$_2$)$_n$—PO$_3{}^{2-}$(X$^{m+}$)$_{1/m}$ or —N$^+$(Me)$_2$-CH$_2$—(CH$_2$)$_n$—SO$_3$, where:
   n is 1, 2, 3 or 4
   X$^{m+}$ is a cation of valence m.

10. The compound according to claim 1 wherein:
   R$^2$ and R$^5$ are the same,
   R$^3$ and R$^6$ are the same, and
   R$^4$ and R$^7$ are the same.

11. The compound according to claim 1 of following formula (Ia):

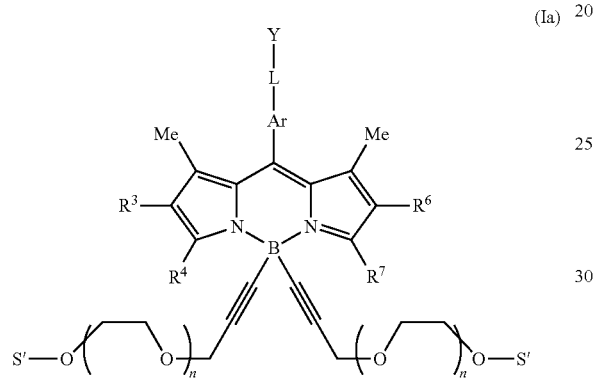

(Ia)

wherein:
   S$^1$ is —H, -Me —(CH$_2$)$_{n'}$—SO$_3{}^-$(X$^{m+}$)$_{1/m}$ or —(CH$_2$)$_{n'}$—PO$_3{}^{2-}$(X$^{m+}$)$_{2/m}$
   in which:
   X$^{m+}$ is a cation (mono- or polyatomic cation) of valence m,
   n' is an integer of 1, 2, 3 or 4,
   Ar is an arylene,
   L is a single bond, a straight or branched alkylene or a substituted straight or branched alkynylene,
   Y is —Cl, —Br, —I, —COOH, —COOMe, —COOEt, —CONH—CH$_2$—CH$_2$—NH$_2$, —CONH—CH$_2$—COOEt, —CONH—CH$_2$—COOH, —CONH—(CH$_2$)$_q$NCS or else a group meeting one of the following formulas:

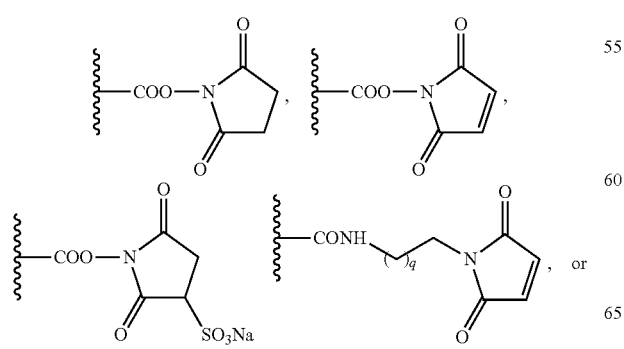

-continued

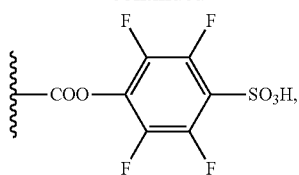

where q is 1, 2, 3, 4 or 5,
   n is 1, 2, 3 or 4,
   R$^3$, R$^6$, R$^4$ and R$^7$ are chosen such that:
      R$^3$ and R$^6$ are the same and represent —H, and R$^4$ and R$^7$ are the same and represent -Me,
      R$^3$ and R$^6$ are the same and represent -Et, and R$^4$ and R$^7$ are the same and represent -Me,
      R$^3$ and R$^6$ are the same and represent —H, and R$^4$ and R$^7$ are the same and represent

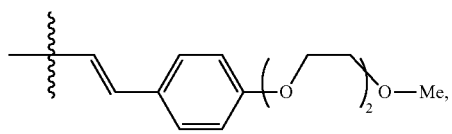

R$^3$ and R$^6$ are the same and represent —H, R$^4$ represents -Me and R$^7$ represents

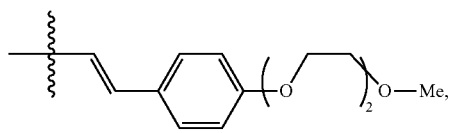

R$^3$ and R$^6$ are the same and represent —H, and R$^4$ and R$^7$ are the same and represent

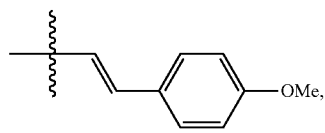

R$^3$ and R$^4$ together form a divalent group —(CH$_2$)$_4$— and R$^6$ and R$^7$ together form a divalent group —(CH$_2$)$_4$—, or
   R$^3$ and R$^6$ are the same and represent —H, R$^4$ represents -Me and R$^7$ represents

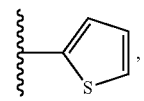

substituted or unsubstituted.

12. The compound according to claim 1 of following formula (Ic):

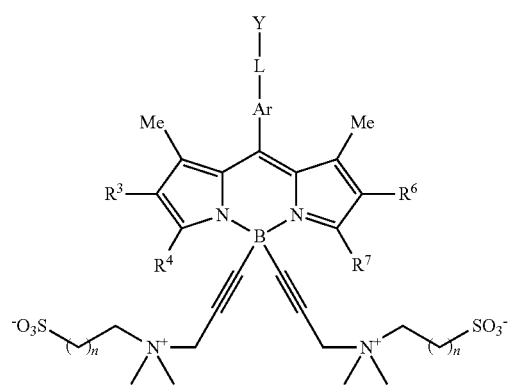

(Ic)

wherein:

Ar is an arylene,

L is a single bond, a straight or branched alkylene or a substituted straight or branched alkynylene, Y is —Cl, —Br, —I, —COOH, —COOMe, —COOEt, —CONH—$CH_2$—$CH_2$—$NH_2$, —CONH—$CH_2$—COOEt, —CONH—$CH_2$—COOH, —CONH—$(CH_2)_q$NCS or else a group meeting one of the following formulas:

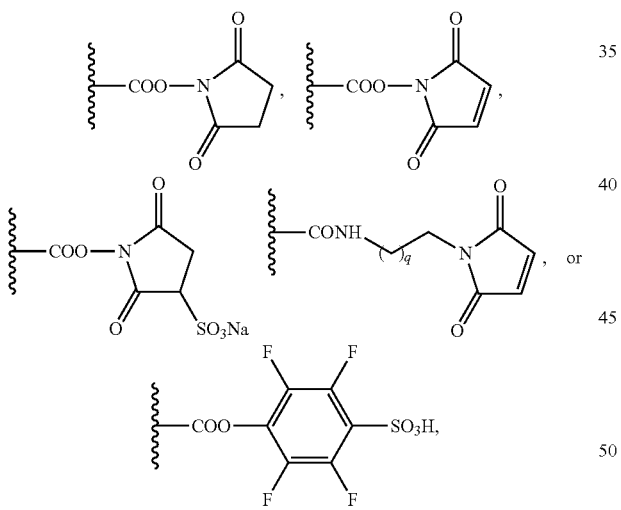

where q is 1, 2, 3, 4 or 5, the groups $R^3$, $R^4$, $R^6$ and $R^7$ are each independently selected from the group consisting of —H, -Me, —C≡C—$CH_2$—$N^+(Me)_2$-$(CH_2)_n$—$SO_3^-$, —C≡C—Ar—R' and a group of formula

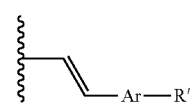

where:

Ar is an arylene,

R' is —OMe, —$CH_2$—$PO_3^{2-}(X^{m+})_{2/m}$ or —C≡C—$CH_2$—R", in which R" is —O—$(CH_2$—$CH_2$—$O)_n$—$CH_3$, —O—$(CH_2$—$CH_2$—$O)_n$—$CH_2$—$PO_3^{2-}(X^{m+})_{2/m}$, —O—$(CH_2$—$CH_2$—$O)_n$—$CH_2$—$SO_3^-(X^{m+})_{1/m}$, —$N^+(Me)_2$-$CH_2$—$(CH_2)_n$—$PO_3^{2-}(X^{m+})_{1/m}$ or —$N^+(Me)_2$-$CH_2$—$(CH_2)_n$—$SO_3$, where:

n is 1 2, 3 or 4

$X^{m+}$ is a cation of valence m, and n is 2, 3 or 4.

13. The compound according to claim 1, having one of the following formulas:

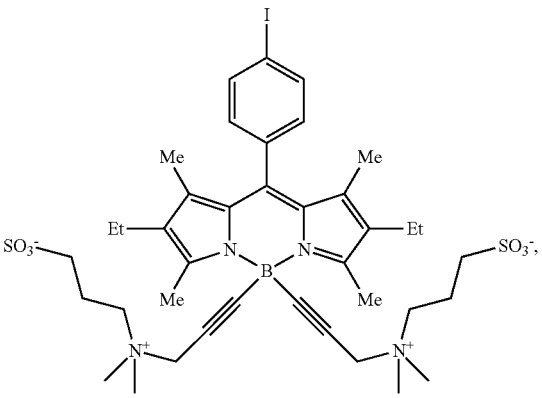

Ic-1

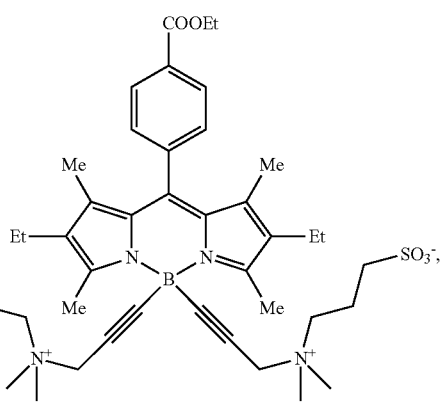

Ic-2

Ic-3
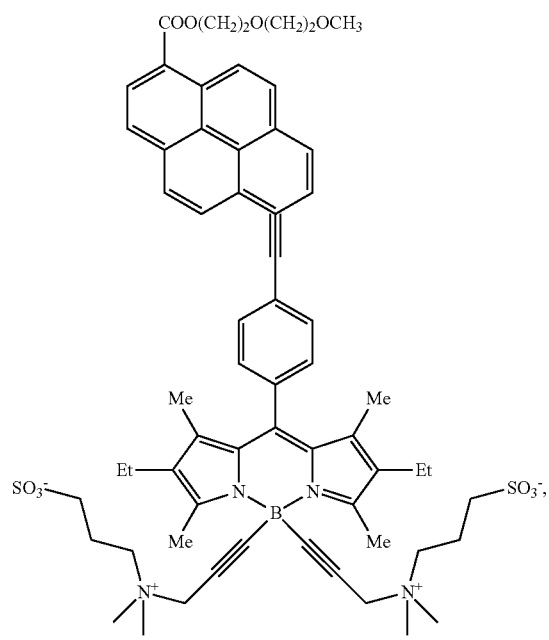
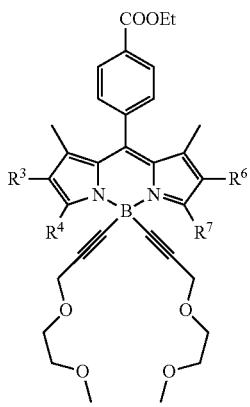
Ia-5 $R^3 = R^6 = H; R^4 = R^7 = Me$
Ia-6 $R^3 = R^6 = Et; R^4 = R^7 = Me$
Ia-7 $R^3 = R^6 = H; R^4 = R^7 =$ 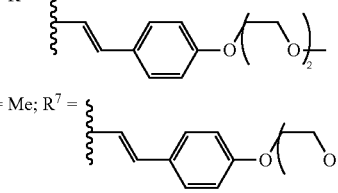
Ia-8 $R^3 = R^6 = H; R^4 = Me; R^7 =$ 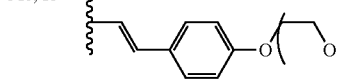
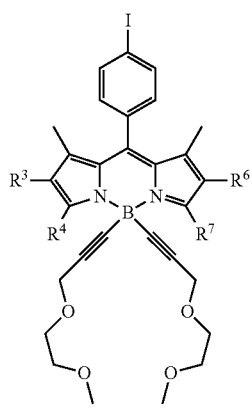
Ia-1 $R^3 = R^6 = H; R^4 = R^7 = Me$
Ia-2 $R^3 = R^6 = Et; R^4 = R^7 = Me$
Ia-3 $R^3 = R^6 = H; R^4 = R^7 =$ 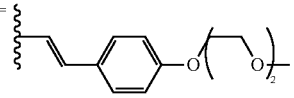
Ia-4 $R^3 = R^6 = H; R^4 = Me; R^7 =$ 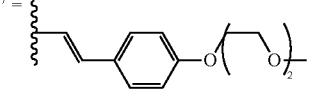
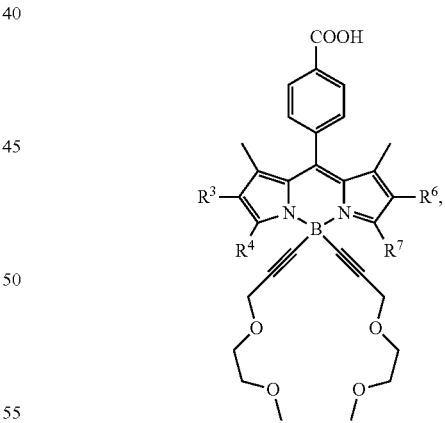
Ia-9 $R^3 = R^6 = H; R^4 = R^7 = Me$
Ia-10 $R^3 = R^6 = Et; R^4 = R^7 = Me$
Ia-11 $R^3 = R^6 = H; R^4 = R^7 =$ 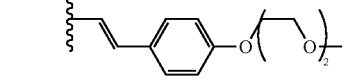
Ia-12 $R^3 = R^6 = H; R^4 = Me; R^7 =$ 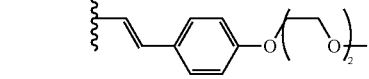

71
-continued
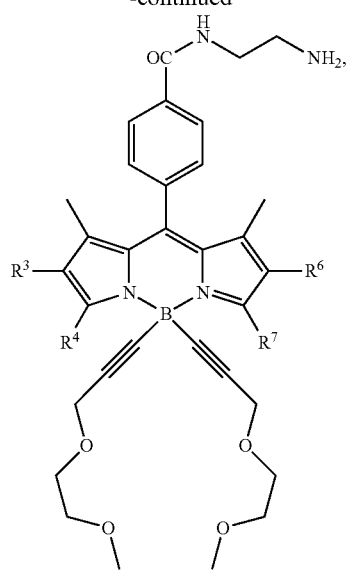
Ia-13 R³ = R⁶ = H; R⁴ = R⁷ = Me
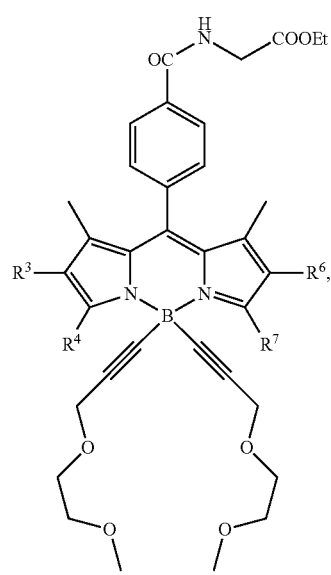
Ia-14 R³ = R⁶ = H; R⁴ = R⁷ = Me
72
-continued
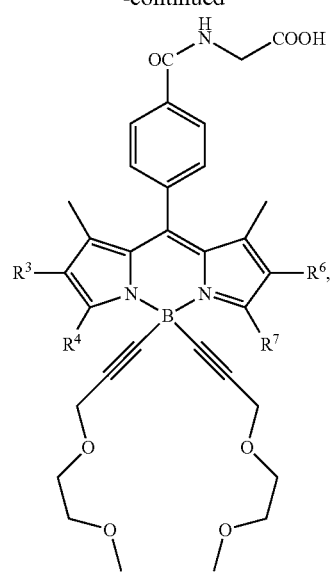
Ia-15 R³ = R⁶ = H; R⁴ = R⁷ = Me
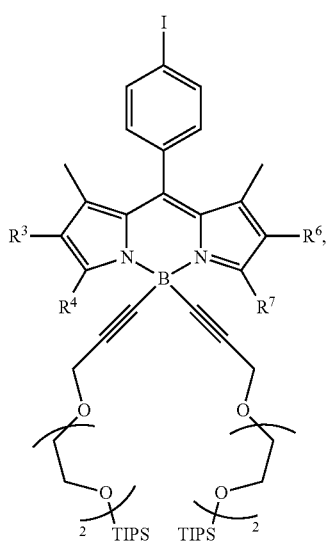
Ia-16 R³ = R⁶ = H; R⁴ = R⁷ = Me 73
-continued
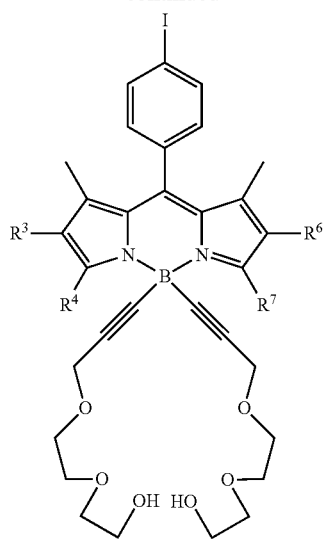
Ia-17 R³ = R⁶ = H; R⁴ = R⁷ = Me
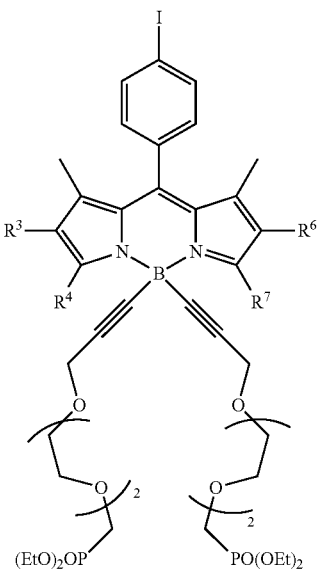
Ia-18 R³ = R⁶ = H; R⁴ = R⁷ = Me
74
-continued
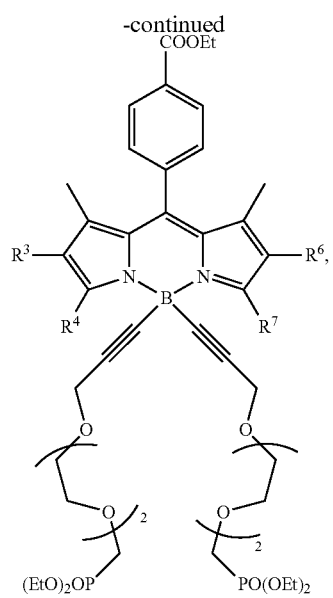
Ia-19 R³ = R⁶ = H; R⁴ = R⁷ = Me   or
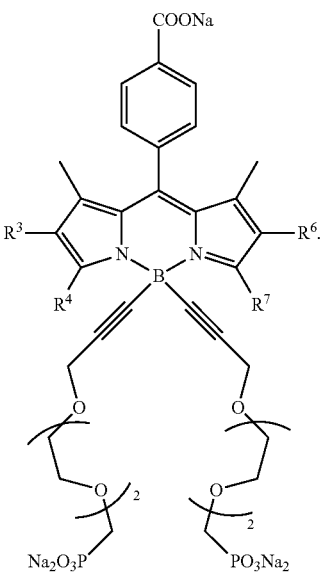
Ia-20 R³ = R⁶ = H; R⁴ = R⁷ = Me 14. The compound according to claim 1 which are water-soluble and meet one of the following formulas:

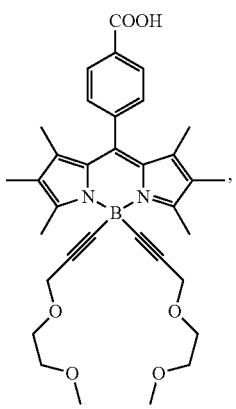

Ia-9 $R^3 = R^6 = H$; $R^4 = R^7 = Me$
Ia-10 $R^3 = R^6 = Et$; $R^4 = R^7 = Me$
Ia-12 $R^3 = R^6 = H$; $R^4 = Me$; $R^7 =$

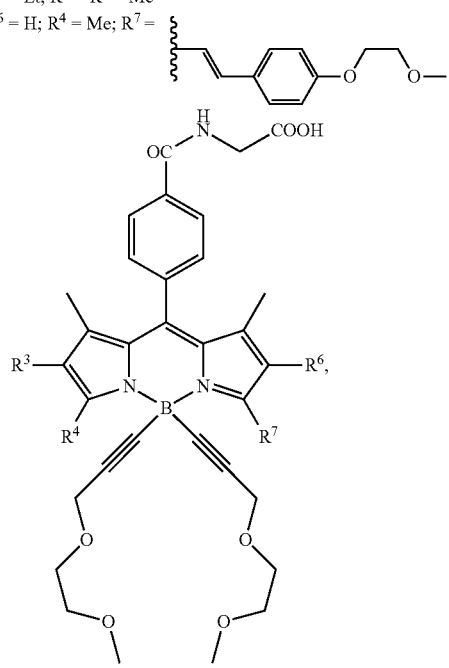

Ia-15 $R^3 = R^6 = H$; $R^4 = R^7 = Me$ or

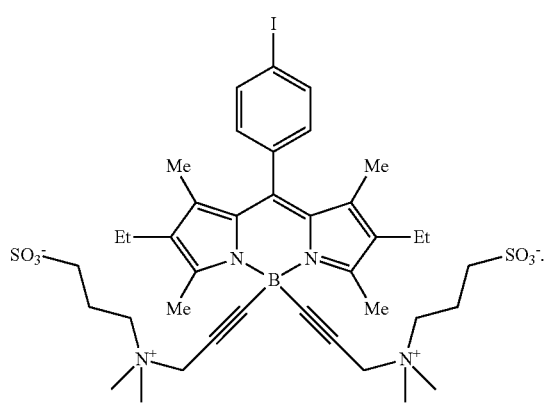

Ic-1

15. A method of conducting fluorescence analysis in an aqueous medium comprising:

(a) providing in an aqueous media a fluorescent and hydrophilic compound meeting following formula (I):

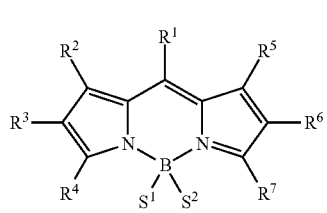

(I)

wherein:

$S^1$ is a group of formula —C≡C-L'-A in which:

L' is a linkage group which is a single bond; or a divalent hydrocarbon group chosen from the group consisting of straight or branched alkylenes optionally comprising one or more oxygen, nitrogen or sulphur atoms in their chain; straight or branched alkenylenes; straight or branched alkynylenes, and arylenes; or a divalent hydrocarbon chain consisting of a chain of at least two divalent hydrocarbon groups of the aforementioned type;

A is a polar functional group chosen from among the sulphonate, sulphate, phosphate, ammonium, carboxylate, hydroxyl, phosphonate, alkylammonium sulphate and polyoxyethylene groups;

$S^2$ is:

a —C≡C-L'-A group the same or different from $S^1$, in which L' and A have the aforementioned meanings;

—F;

—H; or a hydrocarbon chain, straight or branched, saturated or unsaturated, optionally interrupted by one or more oxygen, nitrogen or sulphur atoms, optionally cyclized in whole or in part, optionally aromatic and optionally functionalized; and each of the groups $R^1$, $R^2$, $R^3$, $R^4$, $R^5$, $R^6$ or $R^7$ each independently designates an —H group or a straight or branched, saturated or unsaturated hydrocarbon chain, optionally interrupted by one or more oxygen atoms, optionally cyclized in whole or in part, optionally aromatic and optionally functionalized, on the understanding that all or part of $R^1$, $R^2$, $R^3$, $R^4$, $R^5$, $R^6$ or $R^7$ can be linked together to form a bridged form; and (b) conducting said fluorescence analysis in said aqueous medium.

16. The method of claim 15, wherein said fluorescence analysis is selected from the group consisting of a fluoroimmmunological assay, fluorescence microscopy, flow cytometry, DNA sequencing and the marking of biological material.

* * * * *